(12) United States Patent
Bédard et al.

(10) Patent No.: US 11,571,456 B2
(45) Date of Patent: Feb. 7, 2023

(54) PROCESS FOR THE LINEAR SYNTHESIS OF GRAM-POSITIVE CLASS II BACTERIOCINS AND COMPOSITIONS AND USES THEREOF

(71) Applicant: UNIVERSITÉ LAVAL, Québec (CA)

(72) Inventors: François Bédard, Saint-Augustin-de-Desmaures (CA); Éric Biron, Saint-Augustin-de-Desmaures (CA); Riadh Hammami, Ottawa (CA); Ismail Fliss, Québec (CA)

(73) Assignee: UNIVERSITÉ LAVAL, Québec (CA)

( * ) Notice: Subject to any disclaimer, the term of this patent is extended or adjusted under 35 U.S.C. 154(b) by 0 days.

(21) Appl. No.: 16/616,322

(22) PCT Filed: May 23, 2018

(86) PCT No.: PCT/CA2018/050598
§ 371 (c)(1),
(2) Date: Nov. 22, 2019

(87) PCT Pub. No.: WO2018/213922
PCT Pub. Date: Nov. 29, 2018

(65) Prior Publication Data
US 2021/0023168 A1 Jan. 28, 2021

Related U.S. Application Data

(60) Provisional application No. 62/509,978, filed on May 23, 2017.

(51) Int. Cl.
| | | |
|---|---|---|
| *A61P 31/04* | (2006.01) | |
| *A61K 38/16* | (2006.01) | |
| *A01N 37/46* | (2006.01) | |
| *C07K 1/04* | (2006.01) | |

(52) U.S. Cl.
CPC ............ *A61K 38/164* (2013.01); *A01N 37/46* (2013.01); *A61P 31/04* (2018.01); *C07K 1/04* (2013.01)

(58) Field of Classification Search
CPC ....... A61K 38/164; A61K 38/00; A61P 31/04; A01N 37/46; C07K 1/04; C07K 14/335; A23L 3/34635
See application file for complete search history.

(56) References Cited

PUBLICATIONS

Koo et al. (Proc. KSAM International Symposium, Jun. 20-22, 2001, Chonan, Korea) (Year: 2001).*
Wohr et al (J.Am.Chem.Soc., 1996, 118, 9218-9227) (Year: 1996).*
Abee et al., "Bacteriocins: modes of action and potentials in food preservation and control of food poisoning" *International journal of food microbiology* 1995, 28 (2), 169-85.
Bastos et al., "Resistance to bacteriocins produced by Gram-positive bacteria" *Microbiology* 2015, 161 (Pt 4), 683-700.
Cotter et al., "Bacteriocins—a viable alternative to antibiotics?", *Nature reviews, Microbiology* 2013, 11(2), 95-105.
Derksen et al., "Antimicrobial Leucocin Analogues with a Disulfide Bridge Replaced by a Carbocycle or by Noncovalent Interactions of Allyl Glycine Residues" *JACS* 2006, 128, 14252-14253.
Derksen et al., "Hydrophobic Interactions as Substitutes for a Conserved Disulfide Linkage in the Type IIa Bacteriocins, Leucocin A and Pediocin PA-1" *ChemBioChem* 2008, 9(12), 1898-1901.
Duhan, et al., "Bacteriocins from Lactic Acid Bacteria", Biotechnology: Prospects and Applications *Springer India: New Delhi* 2013, 127-141.
International Search Report and Written Opinion issued in International Application No. PCT/CA2018/050598, dated Jul. 20, 2018.
Johnsen et al., "Engineering Increased Stability in the Antimicrobial Peptide Pediocin PA-1" *Applied and Environmental Microbiology* 2000, 66, 4798-4802.
O'Bryan et al., "Chapter 15—Characteristics of Bacteriocins and Use as Food Antimicrobials in the United States", Food and Feed Safety Systems and Analysis, Academic Press, 273-286, 2018.
Oppegard et al., "The Pediocin PA-1 Accessory Protein Ensures Correct Disulfide Bond Formation in the Antimicrobial Peptide Pediocin PA-1", *Biochemistry* 2015, 54 (19), 2967-2974.
O'Shea et al., "Bactofencin A, a new type of cationic bacteriocin with unusual immunity", *mBio* 2013, 4(6), e00498-13.
Pattabiraman et al., "Rethinking amide bond synthesis", *Nature* 2011, 480(7378), 471-479.
Tiwari et al., "Improved Antimicrobial Activities of Synthetic-Hybrid Bacteriocins Designed from Enterocin E50-52 and Pediocin PA-1", *Applied and environmental microbiology* 2015, 81(5), 1661-7.
Wolska et al., "Synergy Between Novel Antimicrobials and Conventional Antibiotics or Bacteriocins", *Polish Journal of Microbiology* 2012, 61(2), 95-104.

\* cited by examiner

*Primary Examiner* — Sudhakar Katakam
(74) *Attorney, Agent, or Firm* — Norton Rose Fulbright US LLP

(57) ABSTRACT

A process for the linear synthesis of a gram-positive class II bacteriocin or a variant thereof is disclosed herein. The process comprises the stepwise addition of selected amino acids to a solid support; pseudoproline positioning and reopening; and cleavage of the gram-positive class II bacteriocin or the variant thereof from the solid support to provide a linear gram-positive class II bacteriocin or variant thereof; and in situ disulfide bond formation. Various applications and uses of the synthetic bacteriocins are also disclosed. The synthetic process can also be used to synthesize variants of bacteriocins by the selective substitution of one or more amino acids and/or additions and/or deletions of selected amino acids.

18 Claims, 6 Drawing Sheets
Specification includes a Sequence Listing.

PROCESS FOR THE LINEAR SYNTHESIS OF GRAM-POSITIVE CLASS II BACTERIOCINS AND COMPOSITIONS AND USES THEREOF

CROSS REFERENCE TO RELATED APPLICATIONS

This application claims the benefit of U.S. Provisional Application 62/509,978, filed May 23, 2017. The contents of the referenced application are incorporated into the present application by reference.

SEQUENCE LISTING

This application contains a Sequence Listing which has been submitted via EFS-Web and is hereby incorporated by reference in its entirety. Said copy, created on Oct. 12, 2022 is named "LVRYP0007US ST25" and is 17.8 kb in size.

FIELD

The present disclosure broadly relates to a process for the linear synthesis of gram-positive class II bacteriocins, variants thereof, and compositions and uses thereof. More specifically, but not exclusively, the present disclosure broadly relates to a process for the linear synthesis of gram-positive class IIa, IIb, IIc and IId bacteriocins, variants thereof, and compositions and uses thereof. Yet more specifically, but not exclusively, the present disclosure relates to a process for the linear synthesis of pediocin PA-1, variants thereof, and compositions and uses thereof. Yet more specifically, but not exclusively, the present disclosure relates to a process for the linear synthesis of bactofencin A, variants thereof, and compositions and uses thereof. The present disclosure also relates to novel antimicrobial agents.

BACKGROUND

Antibiotic therapy is certainly one of the most important scientific achievements of the twentieth century both in terms of economic and health impacts for animals as well as for humans. However, the abuse of antibiotics, such as by overprescription, has led to an alarming increase in the number of multi-resistant pathogenic strains such as MRSA (Methicillin Resistant *Staphylococcus aureus*), VRE (Vancomycin Resistant Enterococci) and *Clostridium difficile* and the appearance of serious health problems including significant damage to human commensal microflora and certain autoimmune diseases.[1]

The increase in resistance to antibiotics has become a major challenge in the treatment of various bacterial infections. Indeed, the use of large-scale antibiotics has accelerated the emergence of resistance in many bacterial species. In the US alone, according to recent reports by the Centers for Disease Control and Prevention (CDC), there are at least 2 million people suffering from bacterial related infections, and 23000 deaths per year have been reported that are linked to antibiotic-resistant bacteria. In view of the first generations of antibiotics losing their effectiveness, as evidenced by the aforementioned resistance, a substantial amount of research is being dedicated to the discovery and development of novel and alternative antibiotics.

Bacteriocins represent a class of antimicrobial peptides (AMPs) produced by a broad variety of bacteria in order to survive in their respective competitive environments. Potential health risks associated with the use of chemical preservatives, in addition to increased consumer awareness, have led to bacteriocins being given greater consideration as natural antimicrobial agents.[2] The substantial absence of cross-resistance, as well as the faint propensity for the development of resistance, are further factors favoring the use of bacteriocins as antibiotic agents.[3, 4] Moreover, several combinations of bacteriocins and antibiotics have been reported as exhibiting synergistic effects.[5] Furthermore, bacteriocins have been considered for use in both medicine and the food industry. To date, only one bacteriocin (i.e. nisin A; commercialised as Nisaplin®) has been approved by the Food and Drug Administration (FDA) as "Generally Recognized As Safe" (GRAS). The market value of nisin is expected to reach 500 M$ in 2020.

Among the bacteriocins, the class IIa bacteriocins are produced from food grade bacteria, which offer food scientists the possibility of directing or preventing the development of specific bacterial species in food. This can be particularly useful in preservation or food safety applications. Indeed, the class IIa bacteriocins are active against pathogens such as *Listeria monocytogenes* which has a mortality rate as high as 20-30% when infected. Moreover, *Listeria monocytogenes* has been associated with neonatal deaths, fetal demise, severe meningitis and sepsis.

Even though a great many bacteriocins have been sequenced, only very few have actually been chemically synthesized. Indeed, their synthesis represents, and continuous to represent, a significant challenge to the peptide chemist, largely due to their inherent structural complexity and well defined structure activity relationships (SAR).[6] Moreover, purified bacteriocins isolated from fermentation batches remain quite expensive, partly due to a lengthy purification process, prohibiting their commercial-scale exploitation.[7] The development of chemical syntheses provides for the added advantage of enhancing the pharmacological properties of a given bacteriocin (e.g. solubility, stability, potency, activity and bioavailability). Among the class IL bacteriocins, only a very few called "pediocin-like" bacteriocins, have actually been successfully synthesized. Similarly, very few class IIb-e bacteriocins have been successfully synthesized. To that effect, the total synthesis of Pediocin PA-1 and bactofencin A has been previously achieved in extremely low yields (~0.1% overall yield) and only a few analogs have been prepared. Pediocin PA-1 (class IL bacteriocin) is a broad-spectrum lactic acid bacteria bacteriocin that shows a particularly strong activity against *Listeria monocytogenes*. Bactofencin A (class IId bacteriocin), shows strong activity against pathogens *Listeria monocytogenes* and *Staphylococcus aureus*.

The present disclosure refers to a number of documents, the contents of which are herein incorporated by reference in their entirety.

SUMMARY

In an aspect, the present disclosure broadly relates to a process for the linear synthesis of gram-positive class II bacteriocins, variants thereof, and compositions and uses thereof.

In an aspect, the present disclosure broadly relates to novel antibacterial peptides. More specifically, but not exclusively, the present disclosure relates to novel gram-positive class II bacteriocins and variants thereof. Yet more specifically, but not exclusively, the present disclosure relates to a process for the linear synthesis of gram-positive class II bacteriocins, variants thereof and compositions and uses thereof. The present disclosure also relates to a process for the linear synthesis of gram-positive class II bacteriocins comprising a disulfide bond, variants thereof and compositions and uses thereof. The present disclosure also relates to a process for the linear synthesis of pediocin PA-1, variants thereof and compositions and uses thereof. The present disclosure also relates to a process for the linear synthesis of bactofencin A, variants thereof and compositions and uses thereof. In an embodiment of the present disclosure, the process for the linear synthesis of gram-positive class II bacteriocins comprises the use of solid phase peptide synthesis. In a further embodiment of the present disclosure, the process for the linear synthesis of gram-positive class II bacteriocins comprising a disulfide bond includes the use of solid phase peptide synthesis. In a further embodiment of the present disclosure, the process for the linear synthesis of pediocin PA-1 and variants thereof comprises the use of solid phase peptide synthesis. In a further embodiment of the present disclosure, the process for the linear synthesis of bactofencin A and variants thereof comprises the use of solid phase peptide synthesis.

In an aspect, the present disclosure relates to a process for the linear synthesis of a bacteriocin, the process comprising the stepwise addition of selected amino acids to a solid support; pseudoproline positioning and reopening; and cleavage of the bacteriocin from the solid support to provide a linear bacteriocin. In an embodiment of the present disclosure, the process further comprises in situ formation of a disulfide bond. In an embodiment of the present disclosure the bacteriocin is at least one of pediocin PA-1 or bactofencin A.

In an aspect, the present disclosure relates to a process for the linear synthesis of a bacteriocin or a variant thereof, the process comprising the stepwise addition of selected amino acids to a solid support; pseudoproline positioning and reopening; and cleavage of the bacteriocin or variant thereof from the solid support to provide a linear bacteriocin or variant thereof. In an embodiment of the present disclosure, the process further comprises in situ formation of a disulfide bond. In an embodiment of the present disclosure the bacteriocin is at least one of pediocin PA-1 or bactofencin A or variants thereof.

In an aspect, the present disclosure relates to a process for the linear synthesis of a bacteriocin, the process comprising the stepwise addition of selected amino acids to a solid support; pseudoproline positioning and reopening; cleavage of the bacteriocin from the solid support to provide a linear bacteriocin; and disulfide bond formation. In an embodiment of the present disclosure, the disulfide formation occurs in situ. In a further embodiment of the present disclosure the bacteriocin is at least one of pediocin PA-1 or bactofencin A.

In an aspect, the present disclosure relates to a process for the linear synthesis of a bacteriocin or a variant thereof, the process comprising the stepwise addition of selected amino acids to a solid support; pseudoproline positioning and reopening; cleavage of the bacteriocin or variant thereof from the solid support to provide a linear bacteriocin or variant thereof; and disulfide bond formation. In an embodiment of the present disclosure, the disulfide formation occurs in situ. In a further embodiment of the present disclosure the bacteriocin is at least one of pediocin PA-1 or bactofencin A or variants thereof.

In an aspect, the present disclosure relates to a process for the linear synthesis of a bacteriocin, the process comprising the stepwise addition of selected amino acids to a solid support; pseudoproline positioning and reopening; cleavage of the bacteriocin from the solid support to provide a linear bacteriocin; and disulfide bond formation. In an embodiment of the present disclosure, the disulfide formation occurs in situ. In a further embodiment of the present disclosure, the process further comprises treating the linear bacteriocin with a mobile phase comprising an acid. In an embodiment of the present disclosure the bacteriocin is at least one of pediocin PA-1 or bactofencin A.

In an aspect, the present disclosure relates to a process for the linear synthesis of a bacteriocin or a variant thereof, the process comprising the stepwise addition of selected amino acids to a solid support; pseudoproline positioning and reopening; cleavage of the bacteriocin or variant thereof from the solid support to provide a linear bacteriocin or variant thereof; and disulfide bond formation. In an embodiment of the present disclosure, the disulfide formation occurs in situ. In a further embodiment of the present disclosure, the process further comprises treating the linear bacteriocin or variant thereof with a mobile phase comprising an acid. In an embodiment of the present disclosure the bacteriocin is at least one of pediocin PA-1 or bactofencin A or variants thereof.

In an aspect, the present disclosure relates to a process for the linear synthesis of a bacteriocin, the process comprising the stepwise addition of selected amino acids to a solid support; pseudoproline positioning and reopening; cleavage of the bacteriocin from the solid support to provide a linear bacteriocin; and disulfide bond formation. In a further embodiment of the present disclosure, the process further comprises treating the linear bacteriocin with a mobile phase comprising an acid. In a further embodiment of the present disclosure, the disulfide bond formation comprises oxidative coupling of a pair of thiol containing amino acid residues using an oxidant. In a further embodiment of the present disclosure, the disulfide bond formation comprises in situ disulfide bond formation by contacting the bacteriocin with a suitable medium, non-limiting examples of which include bioassays, biological media or a food matrix. In an embodiment of the present disclosure the bacteriocin is at least one of pediocin PA-1 or bactofencin A.

In an aspect, the present disclosure relates to a process for the linear synthesis of a bacteriocin or a variant thereof, the process comprising the stepwise addition of selected amino acids to a solid support; pseudoproline positioning and reopening; cleavage of the bacteriocin or a variant thereof from the solid support to provide a linear bacteriocin or a variant thereof; and disulfide bond formation. In a further embodiment of the present disclosure, the process further comprises treating the linear bacteriocin or a variant thereof with a mobile phase comprising an acid. In a further embodiment of the present disclosure, the disulfide bond formation comprises oxidative coupling of a pair of thiol containing amino acid residues using an oxidant. In a further embodiment of the present disclosure, the disulfide bond formation comprises in situ disulfide bond formation by contacting the bacteriocin or a variant thereof with a suitable medium, non-limiting examples of which include bioassays or biological media. In an embodiment of the present disclosure the bacteriocin is at least one of pediocin PA-1 or bactofencin A or variants thereof.

In an aspect, the present disclosure relates to a process for the linear synthesis of a bacteriocin, the process comprising the stepwise addition of selected amino acids to a solid support; pseudoproline positioning and reopening; cleavage of the bacteriocin from the solid support to provide a linear bacteriocin; and in situ disulfide bond formation. In an embodiment of the present disclosure, the process further comprises treating the linear bacteriocin with a mobile phase comprising an acid. In an embodiment of the present disclosure the bacteriocin is at least one of pediocin PA-1 or bactofencin A.

In an aspect, the present disclosure relates to a process for the linear synthesis of a bacteriocin or variants thereof, the process comprising the stepwise addition of selected amino acids to a solid support; pseudoproline positioning and reopening; cleavage of the bacteriocin or variants thereof from the solid support to provide a linear bacteriocin or variants thereof; and in situ disulfide bond formation. In an embodiment of the present disclosure, the process further comprises treating the linear bacteriocin or variants thereof with a mobile phase comprising an acid. In an embodiment of the present disclosure the bacteriocin is at least one of pediocin PA-1 or bactofencin A or variants thereof.

In an aspect, the present disclosure relates to a process for the linear synthesis of a bacteriocin, the process comprising the stepwise addition of selected amino acids to a solid support; pseudoproline positioning and reopening; cleavage of the bacteriocin from the solid support to provide a linear bacteriocin; and in situ disulfide bond formation. In an embodiment of the present disclosure, the process further comprises treating the linear bacteriocin with a mobile phase comprising an acid. In a further embodiment of the present disclosure, the disulfide bond formation comprises in situ disulfide bond formation by contacting the bacteriocin with a suitable medium, non-limiting examples of which include bioassays or biological media. In an embodiment of the present disclosure the bacteriocin is at least one of pediocin PA-1 or bactofencin A.

In an aspect, the present disclosure relates to a process for the linear synthesis of a bacteriocin or variants thereof, the process comprising the stepwise addition of selected amino acids to a solid support; pseudoproline positioning and reopening; cleavage of the bacteriocin or variants thereof from the solid support to provide a linear bacteriocin or variants thereof; and in situ disulfide bond formation. In an embodiment of the present disclosure, the process further comprises treating the linear bacteriocin or variants thereof with a mobile phase comprising an acid. In a further embodiment of the present disclosure, the disulfide bond formation comprises in situ disulfide bond formation by contacting the bacteriocin or variants thereof with a suitable medium, non-limiting examples of which include bioassays or biological media. In an embodiment of the present disclosure the bacteriocin is at least one of pediocin PA-1 or bactofencin A or variants thereof.

In an aspect, the present disclosure relates to a composition comprising a bacteriocin and a pharmacologically acceptable carrier. In an embodiment of the present disclosure, the bacteriocin is a synthetic bacteriocin. In a further embodiment of the present disclosure, the synthetic bacteriocin is obtained by linear solid phase peptide synthesis. In an embodiment of the present disclosure the bacteriocin is at least one of pediocin PA-1 or bactofencin A.

In an aspect, the present disclosure relates to a composition comprising a bacteriocin or a variant thereof, and a pharmacologically acceptable carrier. In an embodiment of the present disclosure, the bacteriocin or variant thereof is a synthetic bacteriocin. In a further embodiment of the present disclosure, the synthetic bacteriocin or variant thereof is obtained by linear solid phase peptide synthesis. In an embodiment of the present disclosure the bacteriocin is at least one of pediocin PA-1 or bactofencin A or variants thereof.

In an aspect, the present disclosure relates to a method for the prevention and/or treatment of bacterial related infections comprising administering to a subject in need thereof an effective amount of a bacteriocin. In an embodiment of the present disclosure, the bacteriocin is a synthetic bacteriocin. In a further embodiment of the present disclosure, the synthetic bacteriocin is obtained by linear solid phase peptide synthesis. In a further embodiment of the present disclosure, the synthetic bacteriocin comprises a disulfide bond. In an embodiment of the present disclosure the bacteriocin is at least one of pediocin PA-1 or bactofencin A.

In an aspect, the present disclosure relates to a method for the prevention and/or treatment of bacterial related infections comprising administering to a subject in need thereof an effective amount of a bacteriocin or a variant thereof. In an embodiment of the present disclosure, the bacteriocin is a synthetic bacteriocin or variant thereof. In a further embodiment of the present disclosure, the synthetic bacteriocin or a variant thereof is obtained by linear solid phase peptide synthesis. In a further embodiment of the present disclosure, the synthetic bacteriocin or a variant thereof comprises a disulfide bond. In an embodiment of the present disclosure the bacteriocin is at least one of pediocin PA-1 or bactofencin A or a variant thereof.

In an aspect, the present disclosure relates to a method of preserving a food item comprising applying an effective amount of a bacteriocin to the food item. In an embodiment of the present disclosure, the bacteriocin is a synthetic bacteriocin. In a further embodiment of the present disclosure, the synthetic bacteriocin is obtained by linear solid phase peptide synthesis. In a further embodiment of the present disclosure, the synthetic bacteriocin comprises a disulfide bond. In a further embodiment of the present disclosure, the synthetic bacteriocin is applied to the surface of the food item. In a further embodiment of the present disclosure, the synthetic bacteriocin is applied within the food item. In an embodiment of the present disclosure the bacteriocin is at least one of pediocin PA-1 or bactofencin A.

In an aspect, the present disclosure relates to a method of preserving a food item comprising applying an effective amount of a bacteriocin or a variant thereof to the food item. In an embodiment of the present disclosure, the bacteriocin is a synthetic bacteriocin or a variant thereof. In a further embodiment of the present disclosure, the synthetic bacteriocin or a variant thereof is obtained by linear solid phase peptide synthesis. In a further embodiment of the present disclosure, the synthetic bacteriocin or a variant thereof comprises a disulfide bond. In a further embodiment of the present disclosure, the synthetic bacteriocin or a variant thereof is applied to the surface of the food item. In an embodiment of the present disclosure the bacteriocin is at least one of pediocin PA-1 or bactofencin A or a variant thereof.

In an aspect, the present disclosure relates to a bactericidal food preservation composition adapted for coating a food product for preservation thereof, the composition comprising a bacteriocin in an amount effective to kill a pathogenic agent upon contact. In an embodiment of the present disclosure, the bacteriocin is a synthetic bacteriocin. In a further embodiment of the present disclosure, the synthetic bacteriocin is obtained by linear solid phase peptide synthesis. In a further embodiment of the present disclosure, the synthetic bacteriocin comprises a disulfide bond. In an embodiment of the present disclosure the bacteriocin is at least one of pediocin PA-1 or bactofencin A.

In an aspect, the present disclosure relates to a bactericidal food preservation composition adapted for coating a food product for preservation thereof, the composition comprising a bacteriocin or a variant thereof in an amount effective to kill a pathogenic agent upon contact. In an embodiment of the present disclosure, the bacteriocin is a synthetic bacteriocin or a variant thereof. In a further embodiment of the present disclosure, the synthetic bacteriocin or a variant thereof is obtained by linear solid phase peptide synthesis. In a further embodiment of the present disclosure, the synthetic bacteriocin or a variant thereof comprises a disulfide bond. In an embodiment of the present disclosure the bacteriocin is at least one of pediocin PA-1 or bactofencin A or a variant thereof.

In an aspect, the present disclosure relates to an item comprising a surface, wherein the surface comprises an antimicrobial effective amount of a bacteriocin. In an embodiment of the present disclosure, the bacteriocin is a synthetic bacteriocin. In a further embodiment of the present disclosure, the synthetic bacteriocin is obtained by linear solid phase peptide synthesis. In a further embodiment of the present disclosure, the synthetic bacteriocin comprises a disulfide bond. In an embodiment of the present disclosure the bacteriocin is at least one of pediocin PA-1 or bactofencin A. In a further embodiment of the present disclosure, the item is selected from the group consisting of a medical device, medical instrument and medical implement.

In an aspect, the present disclosure relates to an item comprising a surface, wherein the surface comprises an antimicrobial effective amount of a bacteriocin or a variant thereof. In an embodiment of the present disclosure, the bacteriocin is a synthetic bacteriocin or a variant thereof. In a further embodiment of the present disclosure, the synthetic bacteriocin or a variant thereof is obtained by linear solid phase peptide synthesis. In a further embodiment of the present disclosure, the synthetic bacteriocin or a variant thereof comprises a disulfide bond. In an embodiment of the present disclosure the bacteriocin is at least one of pediocin PA-1 or bactofencin A or a variant thereof. In a further embodiment of the present disclosure, the item is selected from the group consisting of a medical device, medical instrument and medical implement.

In an aspect, the present disclosure relates to a kit comprising one or more bacteriocins and one or more applicators. In an embodiment of the present disclosure, the one or more bacteriocins are synthetic bacteriocins. In a further embodiment of the present disclosure, the synthetic bacteriocins are obtained by linear solid phase peptide synthesis. In a further embodiment of the present disclosure, the synthetic bacteriocins comprise a disulfide bond. In an embodiment of the present disclosure the bacteriocin is at least one of pediocin PA-1 or bactofencin A.

In an aspect, the present disclosure relates to a kit comprising one or more bacteriocins or variants thereof and one or more applicators. In an embodiment of the present disclosure, the one or more bacteriocins or variants thereof are synthetic bacteriocins. In a further embodiment of the present disclosure, the synthetic bacteriocins or variants thereof are obtained by linear solid phase peptide synthesis. In a further embodiment of the present disclosure, the synthetic bacteriocins or variants thereof comprise a disulfide bond. In an embodiment of the present disclosure the bacteriocin is at least one of pediocin PA-1 or bactofencin A or variants thereof.

In an aspect, the present disclosure relates to a preservative comprising an effective amount of one or more bacteriocins in a physiological solution or in a food matrix, non-limiting examples of which include milk, yoghurt or cheese. In an embodiment of the present disclosure, the one or more bacteriocins are synthetic bacteriocins. In a further embodiment of the present disclosure, the synthetic bacteriocins are obtained by linear solid phase peptide synthesis. In a further embodiment of the present disclosure, the one or more synthetic bacteriocins comprise a disulfide bond. In a further embodiment of the present disclosure the one or more synthetic bacteriocins include at least one of pediocin PA-1 or bactofencin A.

In an aspect, the present disclosure relates to a preservative comprising an effective amount of one or more bacteriocins or variants thereof in a physiological solution or in a food matrix non-limiting examples of which include milk, yoghurt or cheese. In an embodiment of the present disclosure, the one or more bacteriocins or variants thereof are synthetic bacteriocins or variants thereof. In a further embodiment of the present disclosure, the synthetic bacteriocins or variants thereof are obtained by linear solid phase peptide synthesis. In a further embodiment of the present disclosure, the one or more synthetic bacteriocins or variants thereof comprise a disulfide bond. In a further embodiment of the present disclosure the one or more synthetic bacteriocins include at least one of pediocin PA-1 or bactofencin A or variants thereof.

In an aspect, the present disclosure relates to a food packaging comprising an antimicrobial composition comprising an effective amount of one or more bacteriocins. In an embodiment of the present disclosure, the one or more bacteriocins are synthetic bacteriocins. In a further embodiment of the present disclosure, the synthetic bacteriocins are obtained by linear solid phase peptide synthesis. In a further embodiment of the present disclosure, the one or more synthetic bacteriocins comprise a disulfide bond. In a further embodiment of the present disclosure the one or more synthetic bacteriocins include at least one of pediocin PA-1 or bactofencin A. In yet a further embodiment of the present disclosure, the food packaging is a film, resin, liner, absorbent pad, plastic, shrink bag, shrink wrap, plastic wrap, Styrofoam™, carton, or cellulosic substrate.

In an aspect, the present disclosure relates to a food packaging comprising an antimicrobial composition comprising an effective amount of one or more bacteriocins or variants thereof. In an embodiment of the present disclosure, the one or more bacteriocins or variants thereof are synthetic bacteriocins or variants thereof. In a further embodiment of the present disclosure, the synthetic bacteriocins or variants thereof are obtained by linear solid phase peptide synthesis. In a further embodiment of the present disclosure, the one or more synthetic bacteriocins or variants thereof comprise a disulfide bond. In a further embodiment of the present disclosure the one or more synthetic bacteriocins include at least one of pediocin PA-1 or bactofencin A or variants thereof. In yet a further embodiment of the present disclosure, the food packaging, is a film, resin, liner, absorbent pad, plastic, shrink bag, shrink wrap, plastic wrap, Styrofoam™, carton, or cellulosic substrate.

In an aspect, the present disclosure relates to a synthetic bacteriocin, non-limiting examples of which include bavaricin, bactofencin, helveticin, acidocin, lactocin, lactacin, lacticin, leucocin, lactococcin, pediocin, curvaticin, curvacin, mutacin, mesentericin, plantaricin, streptin or sakacin. In an embodiment of the present disclosure, the synthetic bacteriocin is obtained by linear solid phase peptide synthesis. In a further embodiment of the present disclosure, the synthetic bacteriocin comprises a disulfide bond.

In an aspect, the present disclosure relates to a synthetic bacteriocin or variants thereof, non-limiting examples of which include bavaricin, bactofencin, helveticin, acidocin, lactocin, lactacin, lacticin, nisin, leucocin, lactococcin, pediocin, curvaticin, curvacin, mutacin, mesentericin, plantaricin, streptin or sakacin or variants of any thereof. In an embodiment of the present disclosure, the synthetic bacteriocin or variants thereof is obtained by linear solid phase peptide synthesis. In a further embodiment of the present disclosure, the synthetic bacteriocin or variants thereof comprises a disulfide bond.

In an aspect, the present disclosure relates to synthetic gram-positive class II bacteriocins having a purity ranging from about 85% to about 99.9%. In an aspect, the present disclosure relates to synthetic gram-positive class IIa bacteriocins having a purity ranging from about 85% to about 99.9%. In an aspect, the present disclosure relates to synthetic gram-positive class IIb bacteriocins having a purity ranging from about 85% to about 99.9%. In an aspect, the present disclosure relates to synthetic gram-positive class IIc bacteriocins having a purity ranging from about 85% to about 99.9%. In an aspect, the present disclosure relates to synthetic gram-positive class IId bacteriocins having a purity ranging from about 85% to about 99.9%. In a further embodiment of the present disclosure, the synthetic gram-positive class II bacteriocins are prepared by solid phase peptide synthesis. In a further embodiment of the present disclosure, the synthetic grain-positive class IIa bacteriocins are prepared by linear solid phase peptide synthesis. In a further embodiment of the present disclosure, the synthetic gram-positive class IIb bacteriocins are prepared by linear solid phase peptide synthesis. In a further embodiment of the present disclosure, the synthetic gram-positive class IIc bacteriocins are prepared by linear solid phase peptide synthesis. In a further embodiment of the present disclosure, the synthetic gram-positive class IId bacteriocins are prepared by linear solid phase peptide synthesis. In a further embodiment of the present disclosure, the synthetic gram-positive class II bacteriocins comprise a disulfide bond. In a further embodiment of the present disclosure, the synthetic gram-positive class IIa bacteriocins comprise a disulfide bond. In a further embodiment of the present disclosure, the synthetic gram-positive class IIb bacteriocins comprise a disulfide bond. In a further embodiment of the present disclosure, the synthetic gram-positive class IIc bacteriocins comprise a disulfide bond. In a further embodiment of the present disclosure, the synthetic gram-positive class IId bacteriocins comprise a disulfide bond. In a further embodiment of the present disclosure, the disulfide bond is generated in situ.

In an aspect, the present disclosure relates to synthetic gram-positive class II bacteriocins or variants thereof having a purity ranging from about 85% to about 99.9%. In an aspect, the present disclosure relates to synthetic gram-positive class IIa bacteriocins or variants thereof having a purity ranging from about 85% to about 99.9%. In an aspect, the present disclosure relates to synthetic gram-positive class IIb bacteriocins or variants thereof having a purity ranging from about 85% to about 99.9%. In an aspect, the present disclosure relates to synthetic gram-positive class IIc bacteriocins or variants thereof having a purity ranging from about 85% to about 99.9%. In an aspect, the present disclosure relates to synthetic gram-positive class IId bacteriocins or variants thereof having a purity ranging from about 85% to about 99.9%. In a further embodiment of the present disclosure, the synthetic gram-positive class II bacteriocins or variants thereof are prepared by linear solid phase peptide synthesis. In a further embodiment of the present disclosure, the synthetic gram-positive class IIa bacteriocins or variants thereof are prepared by linear solid phase peptide synthesis. In a further embodiment of the present disclosure, the synthetic gram-positive class IIb bacteriocins or variants thereof are prepared by linear solid phase peptide synthesis. In a further embodiment of the present disclosure, the synthetic gram-positive class IIc bacteriocins or variants thereof are prepared by linear solid phase peptide synthesis. In a further embodiment of the present disclosure, the synthetic gram-positive class IId bacteriocins or variants thereof are prepared by linear solid phase peptide synthesis. In a further embodiment of the present disclosure, the synthetic gram-positive class II bacteriocins or variants thereof comprise a disulfide bond. In a further embodiment of the present disclosure, the synthetic gram-positive class IIa bacteriocins or variants thereof comprise a disulfide bond. In a further embodiment of the present disclosure, the synthetic gram-positive class IIb bacteriocins or variants thereof comprise a disulfide bond. In a further embodiment of the present disclosure, the synthetic gram-positive class IIc bacteriocins or variants thereof comprise a disulfide bond. In a further embodiment of the present disclosure, the synthetic gram-positive class IId bacteriocins or variants thereof comprise a disulfide bond. In a further embodiment of the present disclosure, the disulfide bond is generated in situ.

In an aspect, the present disclosure relates to the solid phase peptide synthesis of linear gram-positive class II bacteriocins. In an aspect, the present disclosure relates to the solid phase peptide synthesis of linear gram-positive class IIa bacteriocins. In an aspect, the present disclosure relates to the solid phase peptide synthesis of linear gram-positive class IIb bacteriocins. In an aspect, the present disclosure relates to the solid phase peptide synthesis of linear gram-positive class IIc bacteriocins. In an aspect, the present disclosure relates to the solid phase peptide synthesis of linear gram-positive class IId bacteriocins. In a further embodiment of the present disclosure, the linear gram-positive class II bacteriocins comprise a disulfide bond. In a further embodiment of the present disclosure, the linear gram-positive class IIa bacteriocins comprise a disulfide bond. In a further embodiment of the present disclosure, the linear gram-positive class IIb bacteriocins comprise a disulfide bond. In a further embodiment of the present disclosure, the linear gram-positive class IIc bacteriocins comprise a disulfide bond. In a further embodiment of the present disclosure, the linear gram-positive class IId bacteriocins comprise a disulfide bond. In a further embodiment of the present disclosure, the disulfide bond is generated in situ.

In an aspect, the present disclosure relates to the solid phase peptide synthesis of linear gram-positive class II bacteriocins or variants thereof. In an aspect, the present disclosure relates to the solid phase peptide synthesis of linear gram-positive class IIa bacteriocins or variants thereof. In an aspect, the present disclosure relates to the solid phase peptide synthesis of linear gram-positive class IIb bacteriocins or variants thereof. In an aspect, the present disclosure relates to the solid phase peptide synthesis of linear gram-positive class IIc bacteriocins or variants thereof. In an aspect, the present disclosure relates to the solid phase peptide synthesis of linear gram-positive class IId bacteriocins or variants thereof. In a further embodiment of the present disclosure, the linear gram-positive class II bacteriocins or variants thereof comprise a disulfide bond. In a further embodiment of the present disclosure, the linear gram-positive class IIa bacteriocins or variants thereof comprise a disulfide bond. In a further embodiment of the present disclosure, the linear gram-positive class IIb bacteriocins or variants thereof comprise a disulfide bond. In a further embodiment of the present disclosure, the linear gram-positive class IIc bacteriocins or variants thereof comprise a disulfide bond. In a further embodiment of the present disclosure, the linear gram-positive class IId bacteriocins or variants thereof comprise a disulfide bond. In a further embodiment of the present disclosure, the disulfide bond is generated in situ.

In an aspect, the present disclosure relates to the linear synthesis of gram-positive class IIa, IIb, IIc or IId bacteriocins. In an embodiment of the present disclosure, the synthesis comprises a solid phase synthesis of a linear peptide. In a further embodiment of the present disclosure, the synthesis comprises a solid phase synthesis of a linear peptide and chemical disulfide bond formation. In a further embodiment of the present disclosure, the synthesis comprises a solid phase synthesis of a linear peptide and in situ disulfide bond formation in a suitable matrix.

In an aspect, the present disclosure relates to the linear synthesis of gram-positive class IIa, IIb, IIc or IId bacteriocins or variants thereof. In an embodiment of the present disclosure, the synthesis comprises a solid phase synthesis of a linear peptide. In a further embodiment of the present disclosure, the synthesis comprises a solid phase synthesis of a linear peptide and chemical disulfide bond formation. In a further embodiment of the present disclosure, the synthesis comprises a solid phase synthesis of a linear peptide and in situ disulfide bond formation in a suitable matrix.

In an aspect, the present disclosure relates to in situ disulfide bond formation. In an embodiment of the present disclosure, disulfide bond formation comprises contacting a linear gram-positive class IIa bacteriocin comprising at least two sulfur containing amino acid residues with a bioassay medium or any other suitable medium. In an embodiment of the present disclosure, disulfide bond formation comprises contacting a linear gram-positive class IIb bacteriocin comprising at least two sulfur containing amino acid residues with a bioassay medium or any other suitable medium. In an embodiment of the present disclosure, disulfide bond formation comprises contacting a linear gram-positive class IIc bacteriocin comprising at least two sulfur containing amino acid residues with a bioassay medium or any other suitable medium. In an embodiment of the present disclosure, disulfide bond formation comprises contacting a linear gram-positive class IId bacteriocin comprising at least two sulfur containing amino acid residues with a bioassay medium or any other suitable medium.

In an aspect, the present disclosure relates to in situ disulfide bond formation. In an embodiment of the present disclosure, disulfide bond formation comprises contacting a linear gram-positive class IIa bacteriocin, or variants thereof, comprising at least two sulfur containing amino acid residues with a bioassay medium or any other suitable medium. In an embodiment of the present disclosure, disulfide bond formation comprises contacting a linear gram-positive class IIb bacteriocin, or variants thereof, comprising at least two sulfur containing amino acid residues with a bioassay medium or any other suitable medium. In an embodiment of the present disclosure, disulfide bond formation comprises contacting a linear gram-positive class IIc bacteriocin, or variants thereof, comprising at least two sulfur containing amino acid residues with a bioassay medium or any other suitable medium. In an embodiment of the present disclosure, disulfide bond formation comprises contacting a linear gram-positive class IId bacteriocin, or variants thereof, comprising at least two sulfur containing amino acid residues with a bioassay medium or any other suitable medium.

In an aspect, the present disclosure relates to a novel antimicrobial agents and uses thereof. In an embodiment, the present disclosure relates to the use of the novel antimicrobial agents for the prevention and/or treatment of bacterial related infections. In further embodiments of the present disclosure, the novel antimicrobial agents are used in applications related to food preservation and food safety. In further embodiments of the present disclosure, the novel antimicrobial agents comprise synthetic gram-positive class IIa, IIb, IIc or IId bacteriocins or variants thereof. In further embodiments of the present disclosure, the novel antimicrobial agents comprise synthetic gram-positive class IIa, IIb, IIe or IId bacteriocins, or variants thereof, comprising a disulfide bond. In a further embodiment of the present disclosure, the gram-positive class IIa, IIb, IIe or IId bacteriocins, or variants thereof, are obtained by linear solid phase peptide synthesis.

Also disclosed in the context of the present disclosure are embodiments 1 to 73. Embodiment 1 is a process for the linear synthesis of a bacteriocin or a variant thereof, the process comprising: stepwise addition of selected amino acids to a solid support; pseudoproline positioning and reopening; and cleavage of the bacteriocin or variant thereof from the solid support to provide a linear bacteriocin or variant thereof. Embodiment 2 is the process of embodiment 1, further comprising disulfide bond formation. Embodiment 2 is the process of embodiment 1 or 2, further comprising treating the linear bacteriocin with a mobile phase comprising an acid.

Embodiment 4 is a process for the linear synthesis of a gram-positive class II bacteriocin or a variant thereof, the process comprising: stepwise addition of selected amino acids to a solid support; pseudoproline positioning and reopening; cleavage of the gram-positive class II bacteriocin or the variant thereof from the solid support to provide a linear gram-positive class II bacteriocin or variant thereof; and disulfide bond formation. Embodiment 5 is the process of embodiment 4, further comprising treating the linear gram-positive class II bacteriocin or variant thereof with a mobile phase comprising an acid. Embodiment 6 is the process of any one of embodiments 2 to 5, wherein the disulfide bond formation comprises coupling a pair of thiol containing amino acid residues. Embodiment 7 is the process of embodiment 6, wherein the disulfide bond formation consists of chemically reacting the pair of thiol containing amino acid residues using an oxidant. Embodiment 8 is the process of embodiment 6, wherein the disulfide bond formation consists of in situ disulfide bond formation by contacting the linear bacteriocin with a suitable medium. Embodiment 9 is the process of embodiment 8, wherein the medium comprises at least one of a bioassay medium or a biological medium. Embodiment 10 is the process of any one of embodiments 6 to 9, wherein the thiol containing amino acids are at least one of cysteine, homocysteine or other amino acids bearing a thiol-containing side-chain. Embodiment 11 is the process of any one of embodiments 1 to 10, wherein the solid support comprises a ChemMatrix resin, a Wang resin, a polystyrene resin, a substituted polystyrene-based resin, a polyamide resin, a polyacrylate resin, a polyacrylamide resin and a polyethylene glycol-based resin. Embodiment 12 is the process of embodiment 11, wherein the solid support further comprises a resin linker. Embodiment 13 is the process of embodiment 12, wherein the resin linker is an HMPB linker, a Wang linker, a Rink amide linker, a PAL linker, a Ramage linker, a Sieber linker, a linker comprising an hydroxyl function or a trityl-based linker. Embodiment 14 is the process of any one of embodiments 3 to 5, wherein the acid comprises at least acetic acid. Embodiment 15 is the process of embodiment 4, wherein the gram-positive class II bacteriocin is a gram-positive class IIa bacteriocin or a variant thereof, a gram-positive class IIb bacteriocin or a variant thereof, a gram-positive class IIc bacteriocin or a variant thereof or a gram-positive class IId bacteriocin or a variant thereof. Embodiment 16 is the process of embodiment 15, wherein the gram-positive class IIa bacteriocin or variant thereof is a pediocin-like bacteriocin or variant thereof. Embodiment 17 is the process of embodiment 15, wherein the gram-positive class IId bacteriocin or variant thereof is a bactofencin-like bacteriocin or variant thereof. Embodiment 18 is the process of any one of embodiments 4 to 17, wherein the variant has at least 80% sequence identity with an unmodified or native reference sequence. Embodiment 19 is the process of any one of embodiments 4 to 18, wherein the variant has at least 85% sequence identity with an unmodified or native reference sequence. Embodiment 20 is the process of any one of embodiments 4 to 19, wherein the variant has at least 90% sequence identity with an unmodified or native reference sequence. Embodiment 21 is the process of any one of embodiments 4 to 20, wherein the variant has at least 95% sequence identity with an unmodified or native reference sequence. Embodiment 22 is the process of any one of embodiments 4 to 21, wherein the variant has at least 99% sequence identity with an unmodified or native reference sequence. Embodiment 23 is the process of any one of embodiments 4 to 17, wherein the variant has at least one of an amino acid substitution, modification, addition or deletion relative to an unmodified or native reference sequence. Embodiment 24 is the process of embodiment 23, comprising at least two amino acid substitutions. Embodiment 25 is the process of embodiment 23, comprising at least three amino acid substitutions. Embodiment 26 is the process of embodiment 23, comprising at least four amino acid substitutions. Embodiment 27 is the process of any one of embodiments 23 to 26, wherein the amino acid substitution comprises substituting at least one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan for any one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan. Embodiment 28 is the process of embodiment 27, wherein the amino acid substitution comprises substituting at least one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan for alanine, leucine, phenylalanine, tryptophan, or serine. Embodiment 29 is the process of embodiment 28, wherein the amino acid substitution comprises substituting at least one of lysine, arginine, histidine, cysteine, valine, tyrosine, asparagine, glycine, methionine, proline, threonine, tryptophan and cysteine for alanine. Embodiment 30 is the process of embodiment 29, wherein the amino acid substitution comprises substituting methionine for leucine. Embodiment 31 is the process of embodiment 29, wherein the amino acid substitution comprises substituting tyrosine for phenylalanine, serine or tryptophan.

Embodiment 32 is a process for the linear synthesis of a gram-positive class II bacteriocin or a variant thereof, the process comprising: stepwise addition of selected amino acids to a solid support; pseudoproline positioning and reopening; cleavage of the gram-positive class II bacteriocin or the variant thereof from the solid support to provide a linear gram-positive class II bacteriocin or variant thereof; and in situ disulfide bond formation. Embodiment 33 is the process of embodiment 32, further comprising treating the linear gram-positive class II bacteriocin or variant thereof with a mobile phase comprising an acid. Embodiment 34 is the process of embodiment 32 or 33, wherein the in situ disulfide bond formation comprises coupling a pair of thiol containing amino acid residues. Embodiment 35 is the process of any one of embodiments 32 to 35, wherein the in situ disulfide bond formation comprises contacting the linear bacteriocin with a suitable medium. Embodiment 36 is the process of embodiment 35, wherein the medium comprises at least one of a bioassay medium or a biological medium. Embodiment 37 is the process of any one of embodiments 34 to 36, wherein the thiol containing amino acids are at least one of cysteine, homocysteine or other amino acids bearing a thiol-containing side-chain. Embodiment 38 is the process of any one of embodiments 32 to 37, wherein the solid support comprises a ChemMatrix resin, a Wang resin, a polystyrene resin, a substituted polystyrene-based resin, a polyamide resin, a polyacrylate resin, a polyacrylamide resin and a polyethylene glycol-based resin. Embodiment 39 is the process of embodiment 38, wherein the solid support further comprises a resin linker. Embodiment 40 is the process of embodiment 39, wherein the resin linker is an HMPB linker, a Wang linker, a Rink amide linker, a PAL linker, a Ramage linker, a Sieber linker, a linker comprising an hydroxyl function or a trityl-based linker. Embodiment 41 is the process of any one of embodiments 33 to 40, wherein the acid comprises at least acetic acid. Embodiment 42 is the process of any one of embodiments 32 to 41, wherein the gram-positive class II bacteriocin is a gram-positive class IIa bacteriocin or a variant thereof, a gram-positive class IIb bacteriocin or a variant thereof, a gram-positive class IIc bacteriocin or a variant thereof or a gram-positive class IId bacteriocin or a variant thereof. Embodiment 43 is the process of embodiment 42, wherein the gram-positive class IIa bacteriocin or variant thereof is a pediocin-like bacteriocin or variant thereof. Embodiment 44 is the process of embodiment 42, wherein the gram-positive class IId bacteriocin or variant thereof is a bactofencin-like bacteriocin or variant thereof. Embodiment 45 is the process of any one of embodiments 32 to 44, wherein the variant has at least 80% sequence identity with an unmodified or native reference sequence. Embodiment 46 is the process of any one of embodiments 32 to 45, wherein the variant has at least 85% sequence identity with an unmodified or native reference sequence. Embodiment 47 is the process of any one of embodiments 32 to 46, wherein the variant has at least 90% sequence identity with an unmodified or native reference sequence. Embodiment 48 is the process of any one of embodiments 32 to 47, wherein the variant has at least 95% sequence identity with an unmodified or native reference sequence. Embodiment 49 is the process of any one of embodiments 32 to 48, wherein the variant has at least 99% sequence identity with an unmodified or native reference sequence. Embodiment 50 is the process of any one of embodiments 32 to 44, wherein the variant has at least one of an amino acid substitution, modification, addition or deletion relative to an unmodified or native reference sequence. Embodiment 51 is the process of embodiment 50, comprising at least two amino acid substitutions. Embodiment 52 is the process of embodiment 50, comprising at least three amino acid substitutions. Embodiment 53 is the process of embodiment 50, comprising at least four amino acid substitutions. Embodiment 54 is the process of any one of embodiments 50 to 53, wherein the amino acid substitution comprises substituting at least one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan for any one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan. Embodiment 55 is the process of embodiment 54, wherein the amino acid substitution comprises substituting at least one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine and tryptophan for alanine, leucine, phenylalanine, tryptophan, or serine. Embodiment 56 is the process of embodiment 55, wherein the amino acid substitution comprises substituting at least one of lysine, arginine, histidine, cysteine, valine, tyrosine, asparagine, glycine, methionine, proline, threonine, tryptophan and cysteine for alanine. Embodiment 57 is the process of embodiment 55, wherein the amino acid substitution comprises substituting methionine for leucine. Embodiment 58 is the process of embodiment 55, wherein the amino acid substitution comprises substituting tyrosine for phenylalanine, serine or tryptophan.

Embodiment 59 is a composition comprising a bacteriocin as obtained by the process of any one of embodiments 1 to 58 and a pharmacologically acceptable carrier. Embodiment 60 is a method for the prevention and/or treatment of bacterial related infections comprising administering to a subject in need thereof an effective amount of a bacteriocin or a variant thereof as obtained by the process of any one of embodiments 1 to 58. Embodiment 61 is a method of preserving a food item comprising applying an effective amount of a bacteriocin or a variant thereof as obtained by the process of any one of embodiments 1 to 58 to the food item. Embodiment 62 is the method of embodiment 61, wherein the bacteriocin is applied to the surface or within the food item. Embodiment 63 is a bactericidal food preservation composition adapted for coating a food product for preservation thereof, the composition comprising a bacteriocin or a variant thereof as obtained by the process of any one of embodiments 1 to 58 in an amount effective to kill a pathogenic agent upon contact. Embodiment 64 is an item comprising a surface, wherein the surface comprises an antimicrobial effective amount of a bacteriocin as obtained by the process of any one of embodiments 1 to 58. Embodiment 65 is the item of embodiment 64, wherein the item is selected from the group consisting of a medical device, medical instrument and medical implement. Embodiment 66 is a kit comprising one or more bacteriocins or variants thereof as obtained by the process of any one of claims 1 to 58 and one or more applicators. Embodiment 67 is a preservative comprising an effective amount of one or more bacteriocins or variants thereof as obtained by the process of any one of embodiments 1 to 58 in a physiological solution. Embodiment 68 is a food packaging comprising an antimicrobial composition comprising an effective amount of one or more bacteriocins or variants thereof as obtained by the process of any one of embodiments 1 to 58. Embodiment 69 is the food packaging of embodiment 68, wherein the food packaging is a film, resin, liner, absorbent pad, plastic, shrink bag, shrink wrap, plastic wrap, Styrofoam™, carton, or cellulosic substrate. Embodiment 70 is the process of any one of embodiments 1 to 58, wherein the bacteriocin or variant thereof is at least one of bavaricin, helveticin, acidocin, lactocin, lactacin, lacticin, leucocin, lactococcin, pediocin, curvaticin, curvacin, mutacin, mesentericin, plantaricin, streptin, sakacin or variants thereof. Embodiment 71 is a synthetic gram-positive class II bacteriocin or a variant thereof, wherein the synthetic gram-positive class II bacteriocin is obtained by linear solid phase peptide synthesis. Embodiment 72 is the synthetic gram-positive class II bacteriocin of embodiment 71, wherein the synthetic gram-positive class II bacteriocin is pediocin PA-1 or variants thereof. Embodiment 73 is the synthetic gram-positive class II bacteriocin of embodiment 71, wherein the synthetic gram-positive class II bacteriocin is bactofencin A or variants thereof.

The foregoing and other advantages and features of the present disclosure will become more apparent upon reading of the following non-restrictive description of illustrative embodiments thereof, given by way of example only with reference to the accompanying drawings/figures.

BRIEF DESCRIPTION OF THE DRAWINGS/FIGURES

Figure 3:
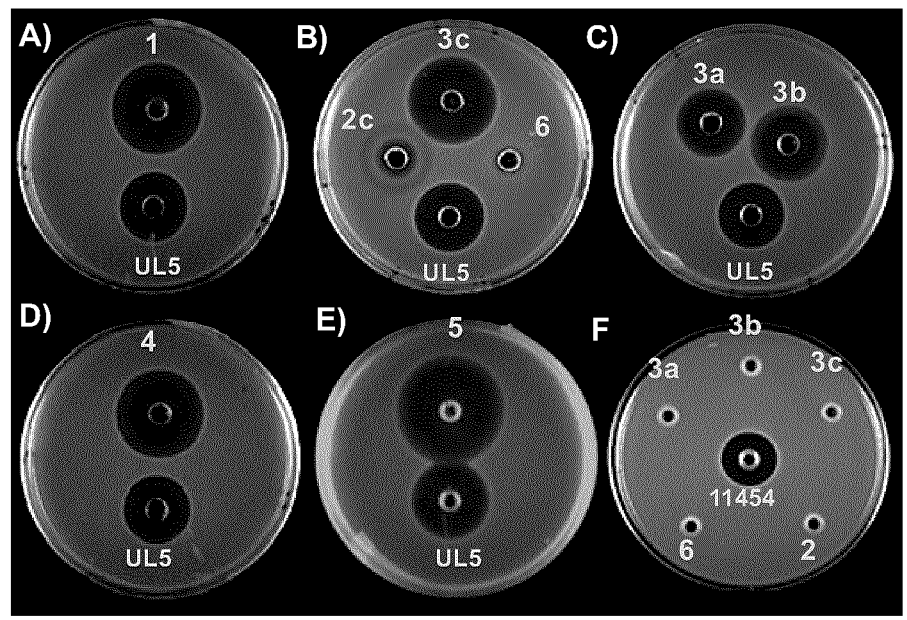

FIG. 3A-F illustrate a soft agar TSBY diffusion growth inhibition assay for native pediocin PA-1 and synthetic variant peptides 2c, 3a, 3b, 3c, 4, 6 against *L. monocytogenes* LSD530. FIG. 3 A-E: 80 µL of supernatant from pediocin PA-1 producing *P. acidilacti* UL5 (24 mm) and 80 µL of a 1 mg/mL solution of: A) 1 (32 mm); B) 2c (14 mm); 3c (31 mm) and 6 (n/a); C) 3a (24 mm) and 3b (27 mm); D) 4 (31 mm); and E) 5 (34 mm). FIG. 3F illustrates a soft agar MRS diffusion growth inhibition assay for 80 µL of supernatant from Nisin producing *L. lactis* ATCC 11454 (18 mm) and 80 µL of synthetic peptides 2c, 3a, 3b, 3c, 4, 6 against *P. acidilacti* UL5.

Figure 4:
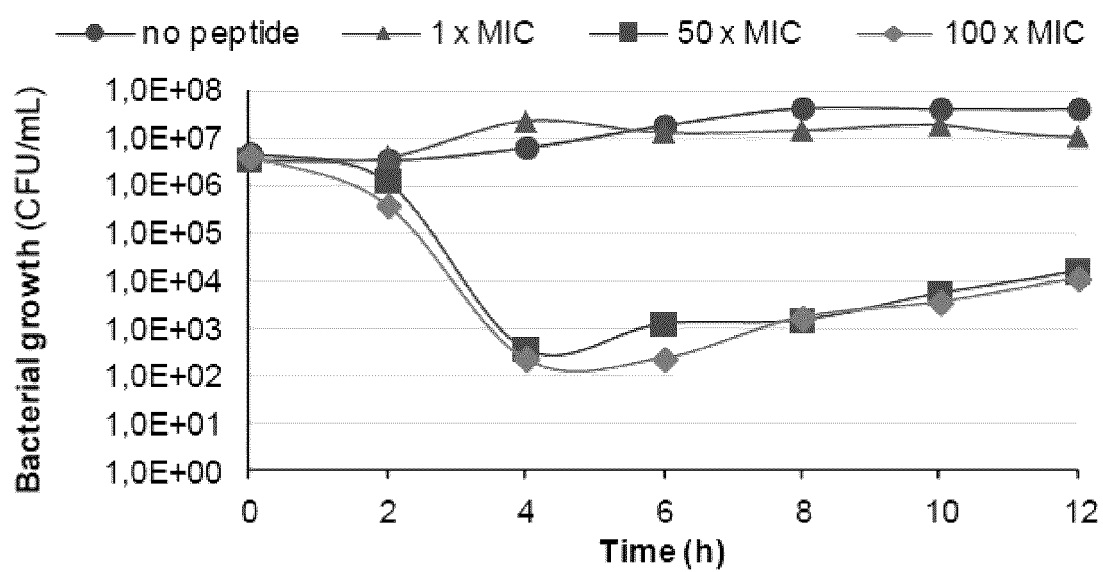

FIG. 4 illustrates the antimicrobial activity of different concentrations of the linear pediocin PA-1 analog 4 in skim milk (10 mL) against *L. monocytogenes* ATCC19111 at 30° C. The average bacterial growth (CFU/mL) for 12 h is shown.

Figure 5:
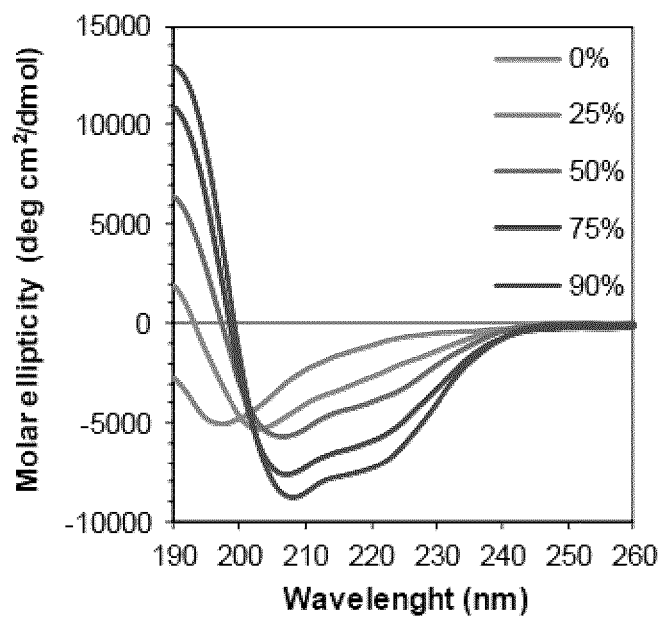
Figure 5:
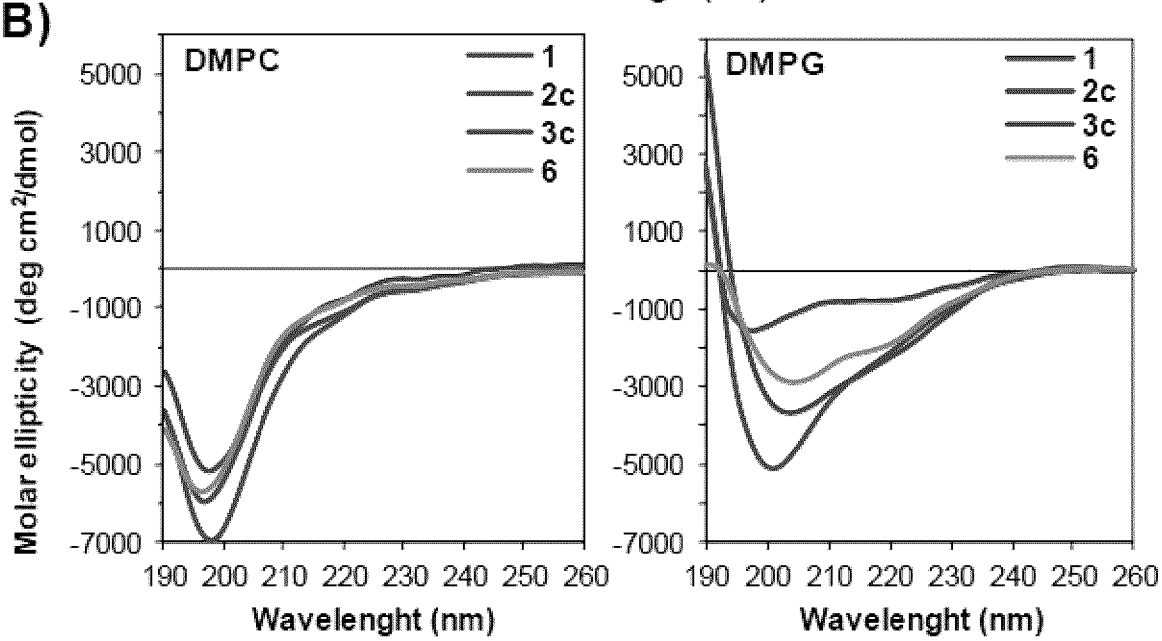

FIG. 5 illustrates circular dichroism spectra obtained for purified pediocin PA-1 3c, linear pediocin PA-1 1 and analogs 2c and 6: A) 3c in aqueous TFE solutions (0, 25, 50, 75 or 90% TFE in $H_2O$) and B) 1, 2c, 3c, and 6 in DMPC (left) and DMPG (right) phospholipid vesicles (lipid/peptide ratio of 10:1).

Figure 6:
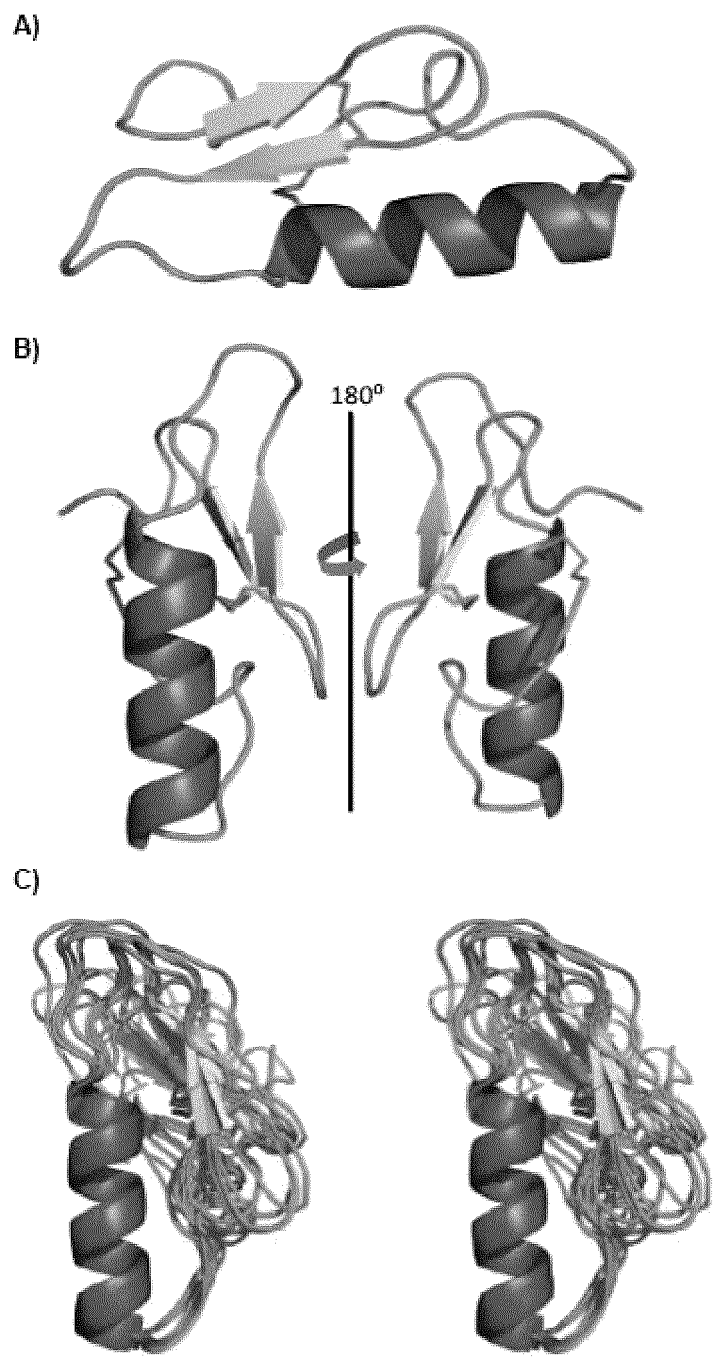

FIG. 6 illustrates the lowest relative energy structure (α-helix red, β-sheet yellow, loops green and disulfide bridge orange) for synthetic pediocin PA-1 analog 5 as determined by $^1$H NMR spectroscopy (50/50 $H_2O$/TFE-d2 at 313° K) (A and B); the lowest energy structures aligned with helix (T23 to T35) (C).

Figure 7:
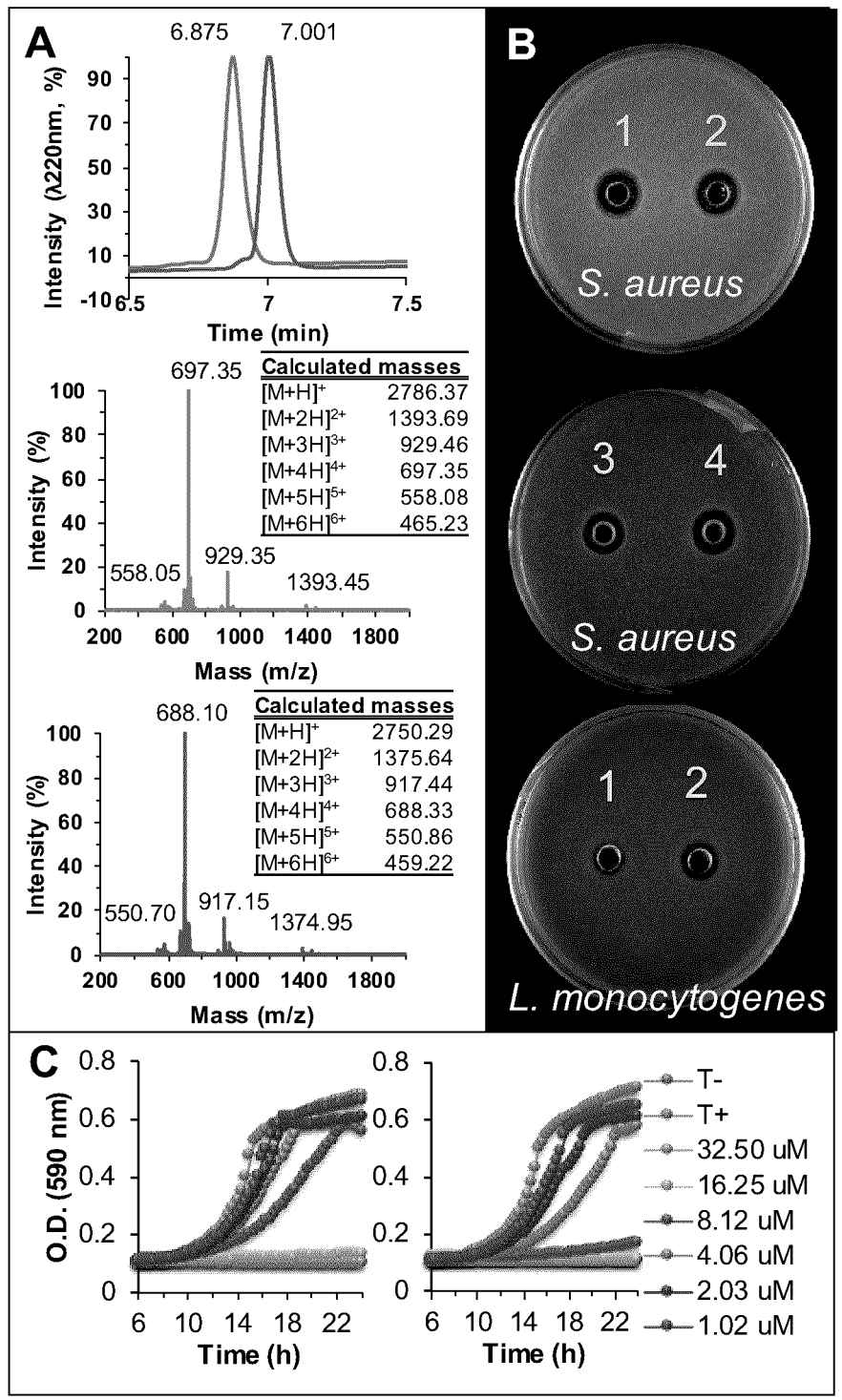

FIG. 7 illustrates the HPLC and ESI-MS profiles of: A) linear sequence bactofencin A and synthetic variant peptide 2 (Table 4); B) soft agar TSBY diffusion growth inhibition assay for linear sequence bactofencin A and synthetic variant peptides 2, 3 and 4 against *S. aureus* ATCC 6538, and linear sequence bactofencin A and synthetic variant peptide 2 against *L. monocytogenes* ATCC 19111; C) activity profiles at various concentrations for linear sequence bactofencin A (left) and synthetic variant peptide 2 (right) against *L. monocytogenes*. ATCC 19111.

DETAILED DESCRIPTION

Glossary

In order to provide a clear and consistent understanding of the terms used in the present disclosure, a number of definitions are provided below. Moreover, unless defined otherwise, all technical and scientific terms as used herein have the same meaning as commonly understood by one of ordinary skill in the art to which this disclosure pertains.

The word "a" or "an" when used in conjunction with the term "comprising" in the claims and/or the disclosure may mean "one", but it is also consistent with the meaning of "one or more", "at least one", and "one or more than one" unless the content clearly dictates otherwise. Similarly, the word "another" may mean at least a second or more unless the content clearly, dictates otherwise.

As used in this disclosure and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this disclosure and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±1% of the modified term if this deviation would not negate the meaning of the word it modifies.

The term "suitable" as used herein means that the selection of the particular compound (e.g. amino acid) and/or reagent (e.g. coupling reagent) and/or conditions would depend on the specific manipulation to be performed, but the selection would be well within the skill of a person trained in the art. All process/method steps described herein are to be conducted under conditions sufficient to provide the product (e.g. peptide) shown. A person skilled in the art would understand that all process/method conditions, including, for example, process/method solvent, process/method time, process/method temperature, process/method pressure, reagent/ingredient ratio and whether or not the process/method should be performed under an anhydrous or inert atmosphere, can be varied to optimize the yield of the desired product and it is within their skill to do so.

The expression "proceed to a sufficient extent" as used herein with reference to the process/method steps disclosed herein means that the process/method steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 99% of the starting material or substrate is converted to product.

The term "analogue" as used herein with reference to the antibacterial peptides refers to a peptide in which one or more individual atoms or functional groups or amino acid residues have been replaced, either with a different atom or a different functional group or a different amino acid residue.

The term "chemical modification" refers to a change in the naturally-occurring chemical structure of one or more amino acids of a polypeptide. Such modifications can be made to a side chain or a terminus, e.g., changing the amino-terminus or carboxyl terminus. In some embodiments, the modifications are useful for creating chemical groups that can conveniently be used to link the polypeptides to other materials.

The term "amino acid" as used herein refers to an organic acid containing both a basic amino group and an acidic carboxyl group. Therefore, the molecule is amphoteric and exists in aqueous solution as dipole ions. In an embodiment of the present disclosure, the amino acids are the L-amino acids. They include but are not limited to the 25 amino acids that have been established as protein constituents. They must contain at least one carboxyl group and one primary or secondary amino group on the amino acid molecule. They include such proteinogenic amino acids as alanine, valine, leucine, isoleucine, norleucine, proline, hydroxyproline, phenylalanine, tryptophan, methionine, glycine, serine, threonine, cysteine, tyrosine, asparagine, glutamine, aspartic acid, glutamic acid, lysine, hydroxylysine, ornithine, arginine, histidine, penicillamine and the like. In an embodiment of the present disclosure, the amino acids are the D-amino acids. In an embodiment of the present disclosure, the amino acids are a mixture of the L- and the D-amino acids.

The term "resin linker" as used herein refers to a molecule attached to the solid support for connecting the peptide chain to the solid support. Linker molecules are generally designed such that eventual cleavage provides either a free acid or amide at the C-terminus. Linkers are generally not resin-specific. The first amino acid of the peptide sequence may be attached to the linker after the linker is attached to the solid support or attached to the solid support using a linker that includes the first amino acid of the peptide sequence.

Conservative changes can generally be made to an amino acid sequence without altering activity. These changes are termed "conservative substitutions"; that is, an amino acid belonging to a grouping of amino acids having a particular size or characteristic can be substituted for another amino acid. Substitutes for an amino acid sequence can be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such substitutions are not expected to substantially affect apparent molecular weight as determined by polyacrylamide gel electrophoresis or isoelectric point. Conservative substitutions also include substituting optical isomers of the sequences for other optical isomers, specifically d amino acids for l amino acids for one or more residues of a sequence. Moreover, all of the amino acids in a sequence can undergo a d to l isomer substitution. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free —NH$_2$. Yet another type of conservative substitution constitutes the case where amino acids with desired chemical reactivities are introduced to impart reactive sites for chemical conjugation reactions, if the need for chemical derivatization arises. Such amino acids include but are not limited to Cys (to insert a sulfhydryl group), Lys (to insert a primary amine), Asp and Glu (to insert a carboxylic acid group). Moreover, substitutions, deletions and insertions of the polypeptide sequences can in some cases be made without a loss of function of the polypeptide. Substitutions can include, e.g., 1, 2, 3, 4, 5, 6, 7, 8, 9, 10, 15 or 20 residues (including any number of substitutions between those listed). A variant of a particular synthetic bacteriocin may exhibit a total number of up to 20 (e.g., up to 1, 2, 3, 4, 5, 6, 7, 8, 9, 10, 15 or 20, including any number in between those listed) changes (e.g., substitutions, deletions, N-terminal and/or C-terminal modifications) in the in the amino acid sequence. In particular embodiments, the variants exhibit about 80%, about 85%, about 90%, about 95%, about 97%, about 98%, about 99% functional equivalence to an unmodified or native reference sequence. The amino acid residues described herein employ either the single letter amino acid designator or the three-letter abbreviation in keeping with the standard polypeptide nomenclature. All amino acid residue sequences are represented herein by formulae with left and right orientation in the conventional direction of amino-terminus to carboxy-terminus.

The term "sequence identity" is used with regard to polypeptide sequence comparisons. This expression in particular refers to a percentage of sequence identity, for example at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide. Particularly, the polypeptide in question and the reference polypeptide exhibit the indicated sequence identity over a continuous stretch of 10, 20, 30, 40, 45, 50, 60, 70, 80, 90, 100 or more amino acids or over the entire length of the reference polypeptide.

In an aspect, the present disclosure relates to the linear synthesis of gram-positive class IIa, IIb, IIc or IId bacteriocins or variants thereof. In an embodiment of the present disclosure, the synthesis comprises a linear solid phase synthesis of gram-positive class IIa, IIb, IIc or Id bacteriocins or variants thereof. In a further aspect, the present disclosure relates to synthetic gram-positive class IIa, IIb, IIc or IId bacteriocins or variants thereof. In yet a further aspect, the present disclosure relates to synthetic gram-positive class IIa, IIb, IIc or IId bacteriocins, or variants thereof, comprising a disulfide bond.

In certain embodiments, the synthetic gram-positive class IIa, IIb, IIc or IId bacteriocin is, is at least, or is at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 amino acids in length (or any range derivable therein).

In an aspect, the present disclosure relates to a process for the linear synthesis of gram-positive class IIa bacteriocins and compositions and uses thereof. In an embodiment, the present disclosure relates to the linear synthesis of pediocin PA-1 and compositions and uses thereof. In a further embodiment of the present disclosure, the synthesis of gram-positive class IIa bacteriocins comprises the use of linear solid phase peptide synthesis. In yet a further embodiment of the present disclosure, the process for the synthesis of pediocin PA-1 comprises the use of linear solid phase peptide synthesis. In yet a further embodiment of the present disclosure, the process for the synthesis of bactofencin A comprises the use of linear solid phase peptide synthesis. In yet a further embodiment of the present disclosure, the various peptides and analogues thereof, were prepared by linear solid phase peptide synthesis using the Fmoc/t-Bu strategy on a HMPB-ChemMatrix® solid support.

The linear synthesis of bacteriocins obviates the need for disulfide formation prior to use. Indeed, large amounts of linear bacteriocins could be produced in high yields at least in view of the absence of a synthetic oxidation step (disulfide bond formation) and an associated purification step. Moreover, the linear synthesis allows for the ready substitution of any amino acid and thus the synthesis of a great many variants of a given bacteriocin.

In an aspect, the present disclosure relates to the linear solid phase peptide synthesis of pediocin PA-1 and variants thereof. It is to be understood that all process/method steps described herein are to be conducted under conditions sufficient to provide the desired end product (e.g. a gram-positive class IIa bacteriocin). A person skilled in the art would understand that all processing conditions, including, for example, processing time, processing temperature, and whether or not the process should be performed under an anhydrous or inert atmosphere, can be varied to optimize the yield of the desired product and it is within their skill to do so.

It will be apparent to one skilled in the art, that in the course of peptide synthesis, it may be necessary to protect certain side chains of the amino acids to prevent unwanted side reactions. For example, it may be necessary to protect the hydroxyl group on the side chain of tyrosine, serine, or threonine in order to prevent these groups from interfering with the desired reactions. This is a common problem in peptide synthesis and many procedures are available for protecting the functional groups on the side chains of the amino acids. Such procedures for protecting various functional groups are known to one skilled in the art and are described in the treatise entitled "PEPTIDES: CHEMISTRY AND BIOLOGY", Norbert Sewald and Hans-Dieter Jakubke, $2^{nd}$ Edition, Wiley-VCH Verlag GmbH & Co., Weinheim, 2009, and the reference book "Protective Groups in Organic Synthesis, $3^{rd}$ Edition, by T.W. Green and P.G.M. Wuts, John Wiley and Sons, New York, 2002, the contents of both being incorporated herein by reference.

In accordance with an embodiment of the present disclosure, and with reference to Scheme 1, there is shown a linear solid phase peptide synthesis of pediocin PA-1. The HMPB-ChemMatrix® solid support was selected to perform the synthesis in view of its higher performance with larger peptides and/or its ability to form aggregation-disrupting interactions with the growing peptide chains. An initial attempt at preparing the linear precursor 1 by stepwise amino acid additions yielded a complex mixture of short peptides while the desired peptide product could not be observed. In order to identify the problematic amino acid couplings, a series of C-terminal ladder sequences starting from Gly40 and working upstream (GNHKC, QGNHKC, etc.) were prepared in parallel and analyzed by HPLC-MS after their cleavage from the resin. The results showed that the coupling of Fmoc-Ala-OH on Gly29 was ineffective. As reported in a previous study on pediocin analogs, pseudo-prolines were incorporated to address these problematic couplings by coupling Fmoc-Val-Thr($\Psi^{Me,Me}$pro)-OH on residue Cys9, and Fmoc-Ala-Thr($\Psi^{Me,Me}$pro)-OH on residues Thr23 and Gly36.[8]. The combined use of the HMPB linker and the ChemMatrix solid support (resin), as well as the positioning of the aforementioned pseudoprolines, provides for the preparation and isolation of linear pediocin PA-1 1 following side-chain deprotection and cleavage from the resin. In an embodiment of the present disclosure, peptide cleavage from the resin is achieved by exposing the resin-bound peptides to a TFA cocktail over a period of time sufficient to yield the crude peptide. In yet a further embodiment of the present disclosure, the resin-bound peptide is contacted with the TFA cocktail over a period ranging from 1 to 5 hours. In yet a further embodiment of the present disclosure, the resin-bound peptide is contacted with the TFA cocktail over a period of 3 hours. In yet a further embodiment of the present disclosure, the peptide is contacted with a second TFA cocktail over a period ranging from 1-3 hours. The crude linear pediocin PA-1 1 was isolated in >90% crude purity. In an embodiment of the present disclosure, the TFA cocktail comprises TFA/TIPS/$H_2O$ (95:2.5:2.5).

In addition to the desired peptide product, HPLC-MS analysis of the crude peptide product illustrated that side-chain alkylated peptides represent a significant source of impurity. It was fortuitously discovered that an initial treatment of the resin-bound peptide with the TFA cocktail, followed by precipitating the released crude peptide in diethyl ether and a further treatment with TFA cocktail substantially avoided the formation of these unwanted alkylated adducts. This observation was corroborated by further HPLC analysis showing only a single signal that was attributed to the desired linear pediocin PA-1 1 (55-70% overall yield).

In a particular embodiment of the present disclosure, the synthetic linear gram-positive class II bacteriocins have a purity ranging from about 85% to about 99.9%. In further embodiments of the present disclosure, the synthetic linear gram-positive class II bacteriocins have a purity of at least 85%, 86%, 87%, 88%, 89%, 90%, 91%, 92%, 93%, 94%, 95%, 96%, 97%, 98% or 99% or any range derivable therein. In a particular embodiment of the present disclosure, the synthetic linear gram-positive class IIa bacteriocins have a purity ranging from about 85% to about 99.9%. In further embodiments of the present disclosure, the synthetic linear gram-positive class IIa bacteriocins have a purity of at least 85%, 86%, 87%, 88%, 89%, 90%, 91%, 92%, 93%, 94%, 95%, 96%, 97%, 98% or 99% or any range derivable therein. In a particular embodiment of the present disclosure, the synthetic linear gram-positive class IIb bacteriocins have a purity ranging from about 85% to about 99.9%. In further embodiments of the present disclosure, the synthetic linear gram-positive class IIb bacteriocins have a purity of at least 85%, 86%, 87%, 88%, 89%, 90%, 91%, 92%, 93%, 94%, 95%, 96%, 97%, 98% or 99% or any range derivable therein. In further embodiments of the present disclosure, the synthetic linear gram-positive class IIc bacteriocins have a purity of at least 85%, 86%, 87%, 88%, 89%, 90%, 91%, 92%, 93%, 94%, 95%, 96%, 97%, 98% or 99% or any range derivable therein. In further embodiments of the present disclosure, the synthetic linear gram-positive class IId bacteriocins have a purity of at least 85%, 86%, 87%, 88%, 89%, 90%, 91%, 92%, 93%, 94%, 95%, 96%, 97%, 98% or 99% or any range derivable therein.

Scheme 1

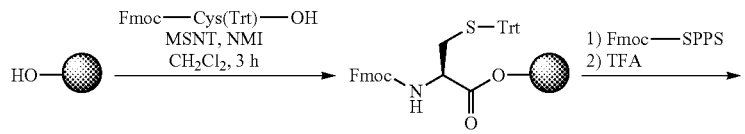

-continued

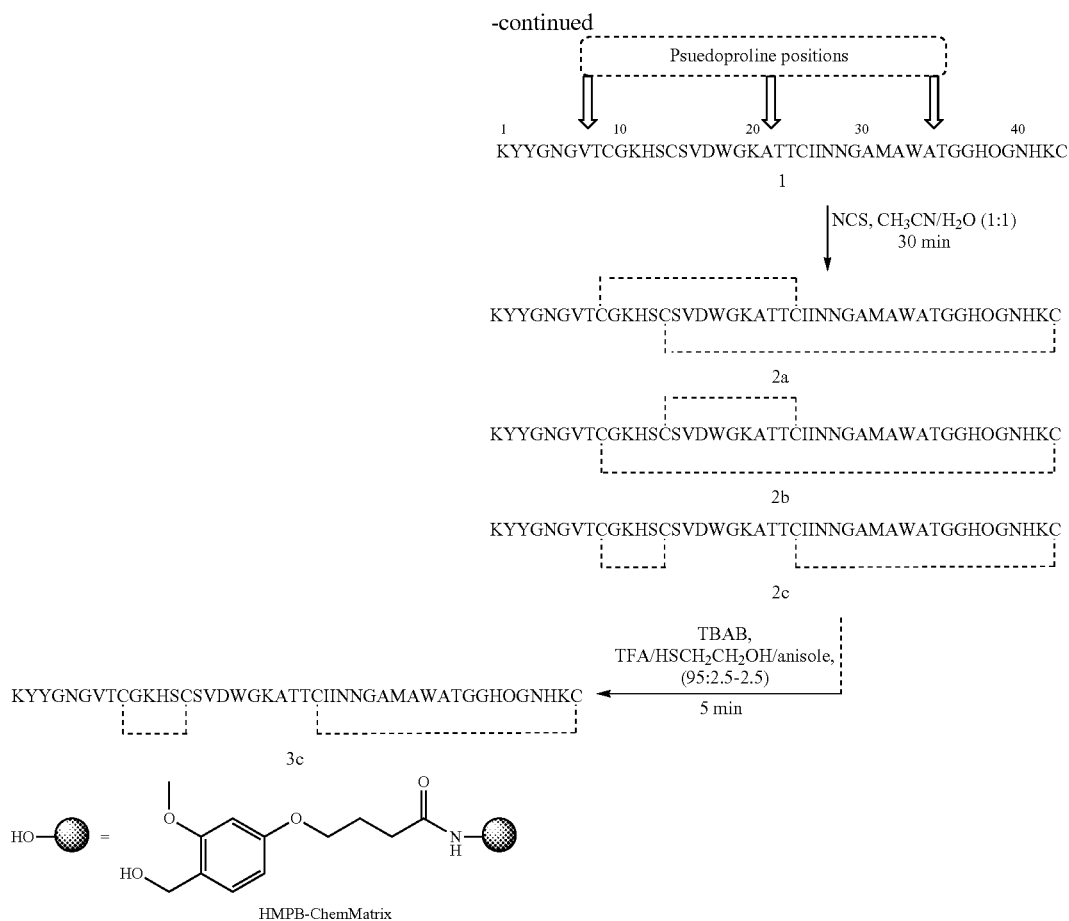

Formation of selective disulfide linkages under mild oxidative conditions generated PA-1 3. Disulfide bond formation however proved to be a challenge in view of the Met31 being very sensitive to oxidation. It was observed that PA-1 2, comprising disulfide linkages between Cys9-Cys24 and Cys14-Cys44 (2a), between Cys9-Cys44 and Cys14-Cys24 (2b), and between Cys9-Cys14 and Cys24-Cys24 (2c), showed no activity. This lack of activity is attributed to the presence of the oxidized Met31 residue. To address the problem associated with the concomitant oxidation of the Met31 residue, it was fortuitously discovered the desired PA-1 3 could be obtained by simultaneous disulfide bond formation and Met31 oxidation using N-chlorosuccinimide (NCS), followed by selective reduction of the Met31 residue using TBAB/TFA/HSCH$_2$CH$_2$OH/Anisole.

Figure 1:
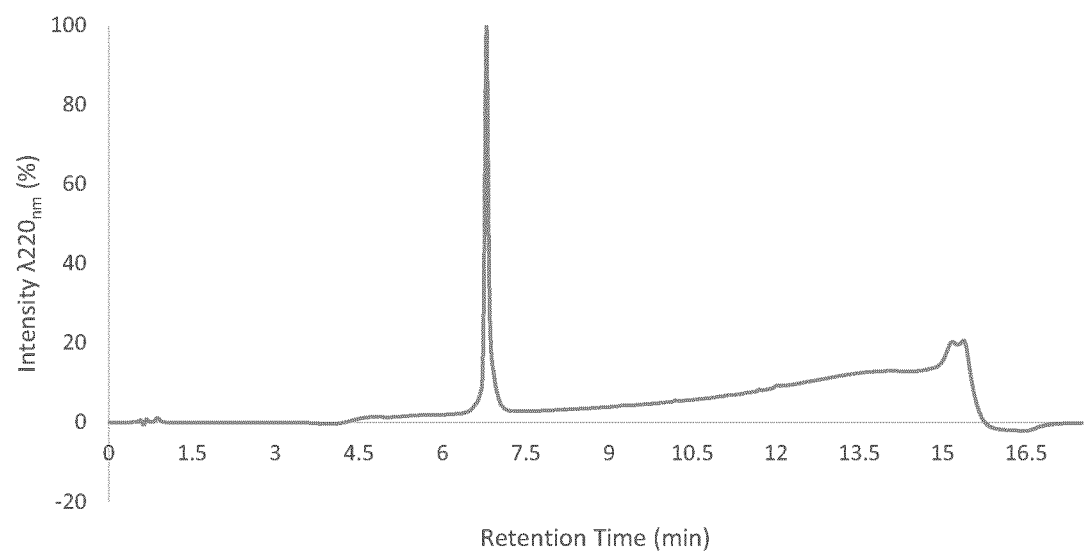
FIG. 1 illustrates the HPLC profile of linear pediocin PA-1 1 as obtained following removal from the solid support in accordance with an embodiment of the present disclosure.
Figure 2:
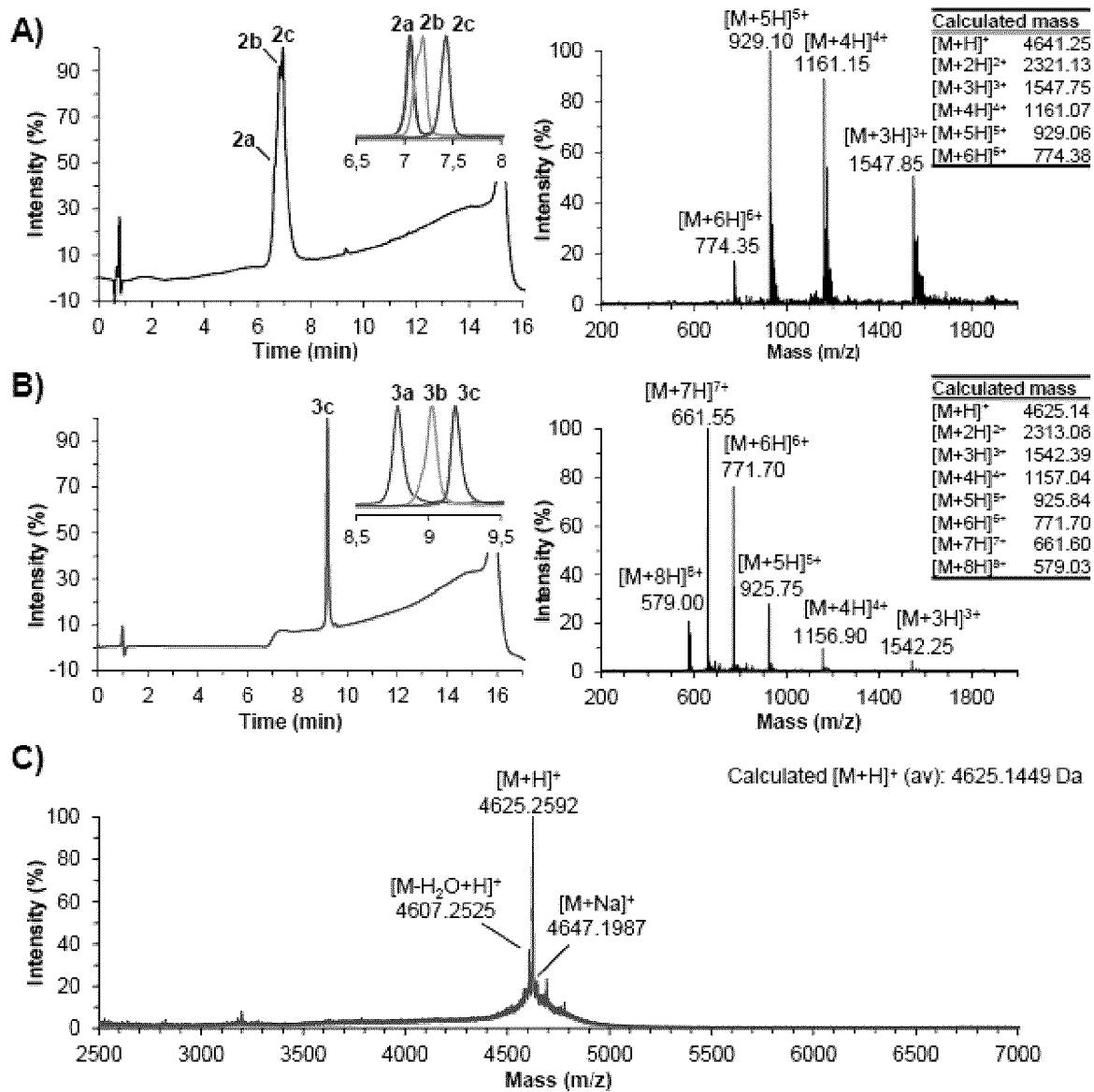
FIG. 2 illustrates the HPLC and ESI-MS profiles of: A) crude oxidized pediocin PA-1 2a, 2b and 2c; B) purified pediocin PA-1 3c; and C) the MALDI-TOF MS spectrum of synthetic pediocin PA-1 3c in accordance with an embodiment of the present disclosure.

Initial attempts at the formation of PA-1 2 from linear precursor PA-1 1 using NCS, resulted in a great number of side products as observed by HPLC. Further analysis of the associated MS and MS/MS spectra revealed that most of the side products comprise peptides having chlorinated aromatic side chains. The presence of such peptide side-products was attributed to the presence of residual TFA counter ions in the purified linear precursor PA-1 1. Such TFA counter ions have been previously reported as catalysts for the chlorination of aromatic residues using NCS. Further purification of the linear precursor PA-1 1 by HPLC, using acetic acid in the mobile phase, resulted in the substantially complete removal of any TFA counter ions from the linear precursor PA-1 1. Indeed, when PA-1 1 was subjected to simultaneous disulfide bond formation and Met31 oxidation using N-chlorosuccinimide (NCS), no chlorinated adducts could be observed. PA-1 2 was obtained as a mixture of 2a (7.5%), 2b (21.5%) and 2c (71.0%) (as determined by HPLC) (FIG. 2A). Subsequent purification by HPLC and MS/MS analysis of the three isolated peptides, provided for the identification of the third peak as that of the oxidized native pediocin PA-1 2c.[10] Reduction of the oxidized Met31 residue at room temperature using tetrabutylammonium bromide (TBAB) in TFA, in the presence of mercaptoethanol (HSCH$_2$CH$_2$OH) and anisole, yielded PA-1 3c. The reduction of the oxidized Met31 residue could be achieved without affecting any of the previously established disulfide bonds. Crude pediocin PA-1 3c was subsequently purified by precipitation in cold diethyl ether.

The presence of synthetic pediocin PA-1 3c was confirmed by HPLC-MS analysis (FIG. 2B) and MALDI-TOF MS (FIG. 2C). MALDI-TOF MS analysis corroborated the presence of synthetic pediocin PA-1 3c as per the observation of a molecular ion, at 4625.2592 Da (calculated[M+H]+ for $C_{196}H_{294}N_{61}O_{60}S_5$: 4625.1449 Da). The amino acid sequence of synthetic pediocin PA-1 3c was subsequently validated by MS/MS following disulfide bond reduction, cysteine S-alkylation using iodoacetamide and trypsin digestion. A similar synthetic process was applied for the synthesis of pediocin PA-1 3a and pediocin PA-1 3b from purified PA-1 2a and PA-1 2b respectively. Table 1 illustrates the peptides synthesized.

TABLE 1

Peptides synthesized.

| ID | SEQ ID NO: | Sequence |
|---|---|---|
| 1 | 1 | KYYGNGVTCGKHSCSVDWGKATTCIINNGAMAWATGGHQGNHK C |
| 2c | 2 | KYYGNGVTCGKHSCSVDWGKATTCIINNGAM(O)AWATGGHQGNHK C (disulfide bonds: Cys—Cys bracketed) |
| 3a | 3 | KYYGNGVTCGKHSCSVDWGKATTCIINNGAMAWATGGHQGNHK C |
| 3b | 4 | KYYGNGVTCGKHSCSVDWGKATTCIINNGAMAWATGGHQGNHK C |
| 3c | 5 | KYYGNGVTCGKHSCSVDWGKATTCIINNGAMAWATGGHQGNHK C |
| 4 | 6 | KYYGNGVTCGKHSCSVDWGKATTCIINNGALAWATGGHQGNHK C |
| 5 | 7 | KYYGNGVTCGKHSCSVDWGKATTCIINNGALAWATGGHQGNHK C |
| 6 | 8 | KYYGNGVTAGKHSASVDWGKATTAIINNGAMAWATGGHQGNHK A |
| 7 | 9 | KRKKHRCRVYNNGMPTGMYRWC |
| 8 | 10 | KRKKHRCRVYNNGLPTGLYRWC |
| 9 |  | H$_2$N-PedM31L-CONH$_2$ |
| 10 |  | Ac-NH-PedM31L-CONH$_2$ |

To avoid the oxidation of the Met31 residue during the synthesis, antibacterial assays and conformational studies, a linear analog of pediocin PA-1 (4) containing a Leu31 residue was prepared as described above. Following purification as described above, pediocin PA-1 4 was obtained in 40% overall yield. Pediocin PA-1 4 was subsequently submitted to disulfide bond formation using NCS to afford pediocin PA-1 and analogue 5 (PA-1 M31L). A reduction protocol was obviated in view of the peptide not containing a Met31 residue.

To demonstrate the importance of the disulfide bonds to the antimicrobial activity of pediocin PA-1 and to maintain its bioactive conformation, a further pediocin PA-1 analog (6) was prepared as described above. Relative to pediocin PA-1 3, pediocin PA-1 6 comprises alanine residues Ala9, Ala14, Ala24 and Ala44. In essence, the Cys residues in PA-1 3 were substituted for Ala residues in PA-1 6.

The antimicrobial activity of pediocin PA-1 1, 2a, 3a-c and pediocin analogues 4 and 6 was assessed by determining the minimal inhibitory concentration against *Listeria ivanovii* HPB28, *Listeria monocytogenes* LSD530, *Listeria monocytogenes* ATCC 19111, *Micrococcus luteus* ATCC 10240 and *Pediococcus acidilacti* UL5. The observed respective minimal inhibitory concentrations are given in Table 2. Synthetic pediocin PA-1 3c showed strong activity with a low nanomolar MIC of 6.75 nM against *L. ivanovii* HPB28 and *L. monocytogenes* LSD530 respectively, and a nanomolar MIC of 13.5 nM against *L. monocytogenes* ATCC 19111. Compared to PA-1 3c, PA-1 3a and 3b, the latter two peptides having an incorrect disulfide bond pairing, showed a 2- to 4-fold decrease in activity against *Listeria ivanovii* HPB28, *Listeria monocytogenes* LSD530 and *Listeria monocytogenes* ATCC 19111 (MIC ranging from 13.5-27.0 nM). The enhanced antimicrobial activity of PA-1 3c relative to PA-1 3a and 3b, could at least in part be explained by PA-1 3c exhibiting an energetically more favorable conformation. Indeed, as per the observed mixture of 2a (7.5%), 2b (21.5%) and 2c (71.5%), there appears to be a thermodynamic equilibrium in the disulfide pairings favoring the conformation exhibited by PA-1 3c. As expected, a significant decrease of antimicrobial activity was observed for PA-1 2a comprising an oxidized Met31 residue. PA-1 2a exhibited an MIC of 1562 nM against *Listeria ivanovii* HPB28 and *Listeria monocytogenes* LSD530, and an MIC of 25000 nM against *Listeria monocytogenes* ATCC 19111. These results confirm that the oxidation of the Met31 residue is detrimental to the activity of PA-1.

TABLE 2

Minimal inhibitory concentrations (MIC) of synthetic
Pediocin PA-1 3c and analogues for selected bacteria.

| Strain | Minimal Inhibitory Concentration (nM) | | | | | | | | | |
|---|---|---|---|---|---|---|---|---|---|---|
| | 1 | 2c | 3a | 3b | 3c | 4 | 5 | 6 | 9 | 10 |
| Listeria ivanovii HPB28 | 6.8 | 1562 | 27.0 | 13.5 | 6.8 | 6.8 | 1.7 | N/A [1] | N/A | N/A |
| Listeria monocytogenes LSD530 | 13.5 | 1562 | 27.0 | 13.5 | 6.8 | 13.5 | 6.8 | N/A | N/A | N/A |
| Listeria monocytogenes ATCC 19111 | 13.5 | 25000 | 27.0 | 13.5 | 13.5 | 13.5 | 13.5 | N/A | 90.0 | 1000 |
| Micrococcus luteus | N/A | N/A | N/A | N/A | N/A | N/A | N/A | N/A | N/A | N/A |
| P. acidilacti UL5 | N/A | N/A | N/A | N/A | N/A | N/A | N/A | N/A | N/A | N/A |

[1] (—) No activity detected at concentrations up to 100 μM.

Surprisingly, linear pediocin PA-1 1 and linear analogue 4 showed similar antimicrobial activity in radial diffusion and microplate dilution assays. Interestingly, these results suggest that the disulfide bonds can be suitably formed in situ in the bioassay medium, without the help of chaperone-like proteins.[5] The observed increased antimicrobial activity of linear pediocin PA-1 1 relative to PA-1 3c, could at least in part be explained by the presence of the free Cys residues acting as oxidant scavengers, preventing the oxidation of the Met31 during disulfide bond formation. The observed antimicrobial activity for linear analog 4 is in agreement with the MIC values previously reported.[9] Regarding PA-1 3c, it is possible that a small amount of Met31 gets oxidized during the assay, thus decreasing its antimicrobial activity. No antimicrobial activity was observed for linear analog 6, indicative of the disulfide bonds being essential for the activity of pediocin PA-1. Even though antimicrobial activity of pediocin PA-1 against *Micrococcus luteus* has recently been reported[12], no activity against *M. luteus* ATCC 10240 could be observed for synthetic pediocin PA-1 3c, PA-1 3a, 3b and linear analogues 4 and 6 at up to 100 μM. It is surmised that this could be the result of low agitation of the cells which need to be oxygenated or again fast methionine oxidation. Finally, none of the synthesized peptides showed antimicrobial activity against *P. acidilacti* UL5.

In order to confirm the results as obtained in the MIC assay, the antibacterial activity of the synthetized peptides was further assessed by radial diffusion assays against *L. monocytogenes* LSD530 and compared to native pediocin PA-1 produced by *P. acidilacti* UL5 (FIG. 3). In agar plate assays against *L. monocytogenes* LSD530, the presence of pediocin PA-1 in the supernatant of *P. acidilacti* UL5 was confirmed by the observed antimicrobial activity with an inhibition diameter of 24 mm (FIG. 3A-D). As expected, synthetic pediocin PA-1 3c showed a substantial inhibition diameter of 31 mm while poor and no activity was observed for analogs 2c and 6, respectively (FIG. 3A). As previously observed with the MIC assay, reduced activity was observed for PA-1 3a and PA-1 3b exhibiting inhibition diameters of 24 and 27 mm, respectively (FIG. 3B). Linear pediocin PA-1 1 and linear analogue 4 exhibited excellent antimicrobial activity as per the observed inhibition diameters of 32 mm (FIGS. 3C and 3D). These results again suggest in situ disulfide bond formation for PA-1 1 and linear analogue 4.[5] Finally, none of the synthetic peptides 2c, 3a-c, and 6 shows antimicrobial activity against *P. acidilacti* UL5 (FIG. 3F)

To corroborate the possibility of in situ disulfide bond formation, bactofencin A (BAC221) linear analogs 7 and 8 were prepared as described above and evaluated in the radial diffusion assay (FIG. 3E). Bactofencin A, a bacteriocin isolated from a porcine intestinal bacteria *Lactobacillus salivarius* DPC6502, and consisting of a short 22 residue, defensin-like sequence, including a disulfide bridge and a methionine residue, is known to be active against both *L. monocytogenes* and *Staphylococcus aureus*.[11] Bactofencin A linear analogs 7 and 8 exhibited inhibition diameters of 9 and 11 mm, respectively against *L. monocytogenes* ATCC 19111. These results are in accordance with previously reported inhibition diameters for native bactofencin A against the aforementioned strains. These results again support in situ disulfide bond formation and further suggest that the Met residues mostly function as hydrophobic residues in the class II bacteriocin mechanism of action. Moreover, the Met18 residue of analogue 7 can be replaced with a Leu18 (analogue 8) enhancing the stability of the peptide.

Synthetic bactofencin A linear analogs 7 and 8 exhibited low micromolar MIC values of 5.8 μM and 2.8 μM against *S. aureus* ATCC 6538 and *L. monocytogenes* ATCC 19111, respectively (Table 3).

TABLE 3

Minimal inhibitory concentrations (MIC) of
synthetic Bactofencin A linear analogs 7 and 8.

| | Minimal Inhibitory Concentration (μM)* | |
|---|---|---|
| Strain | 7 | 8 |
| Listeria monocytogenes ATCC 19111 | 8.02 | 4.06 |
| Staphylococcus aureus ATCC 6538 | 4.01 | 2.00 |

*Initial Concentration 0.25 mg/mL

To evaluate the in situ disulfide bond formation in a biological matrix, the antimicrobial activity of different concentrations of linear pediocin PA-1 analog 4 against *L. monocytogenes* ATCC19111 at 30° C. was assessed in skim milk. The average bacterial growth, (CFU/mL) for 12 h is shown (FIG. 4).

Circular dichroism experiments were performed (FIG. 5) in order to determine the optimal conditions for the $^1$H NMR spectroscopy studies of the peptides. A solvent mixture composed of trifluoroethanol (TFE-d2) and $H_2O$ (50/50) was used for the $^1$H NMR structure analyses. The pH of the solution was maintained under a value of 3 in order to maintain the disulfide bridges in the appropriate pairings. Moreover, Pediocin PA-1 M31L 5 was used in order to prevent oxidation and structural changes during the acquisition times. Moreover, leucine is well known to mimic the electrostatic surface of the methionine. One-dimensional $^1$H NMR and two-dimensional homonuclear $^1$H-$^1$H total correlation spectroscopy (TOCSY) and nuclear Oyerhauser effect spectroscopy (NOESY) data sets were acquired. FIG. 6 illustrates the lowest relative energy structure (α-helix red, β-sheet yellow, loops green and disulfide bridge orange) for synthetic pediocin PA-1 analog 5 as determined by $^1$H NMR spectroscopy.

In an aspect, the present disclosure relates to a process for the linear synthesis of gram-positive class IId bacteriocins and compositions and uses thereof. In an embodiment, the present disclosure relates to the linear synthesis of bactofencin A and compositions and uses thereof. In a further embodiment of the present disclosure, the synthesis of gram-positive class IId bacteriocins comprises the use of linear solid phase peptide synthesis. In yet a further embodiment of the present disclosure, the process for the synthesis of bactofencin A comprises the use of linear solid phase peptide synthesis. In yet a further embodiment of the present disclosure, the various peptides and analogues thereof, were prepared by solid phase peptide synthesis using the Fmoc-Na/t-Bu strategy on a HMPB-ChemMatrix® solid support or Rink-ChemMatrix® solid support.

In an aspect, the present disclosure relates to the linear solid phase peptide synthesis of bactofencin A and variants thereof. It is to be understood that all process/method steps described herein are to be conducted under conditions sufficient to provide the desired end product (e.g. a gram-positive class IId bacteriocin). A person skilled in the art would understand that all processing conditions, including, for example, processing time, processing temperature, and whether or not the process should be performed under an anhydrous or inert atmosphere, can be varied to optimize the yield of the desired product and it is within their skill to do so.

It will be apparent to one skilled in the art, that in the course of peptide synthesis, it may be necessary to protect certain side chains of the amino acids to prevent unwanted side reactions. For example, it may be necessary to protect the hydroxyl group on the side chain of tyrosine, serine, or threonine in order to prevent these groups from interfering with the desired reactions. This is a common problem in peptide synthesis and many procedures are available for protecting the functional groups on the side chains of the amino acids. Such procedures for protecting various functional groups are known to one skilled in the art and are described in the treatise entitled "PEPTIDES: CHEMISTRY AND BIOLOGY", Norbert Sewald and Hans-Dieter Jakubke, $2^{nd}$ Edition, Wiley-VCH Verlag GmbH & Co., Weinheim, 2009, and the reference book "Protective Groups in Organic Synthesis, $3^{rd}$ Edition, by T.W. Green and P.G.M. Wuts, John Wiley and Sons, New York, 2002, the contents of both being incorporated herein by reference.

Straight forward Fmoc-Na/t-Bu solid phase peptide synthesis (SPPS) on a HMPB and Rink-ChemMatrix®, Rink AM and 2-Chlorotrityl polystyrene resin provided for the linear synthesis of Bactofencin A as well as variants thereof (Table 4).

TABLE 4

Bactofencin A and variants thereof and their activity against S. aureus ATCC 6538 cultivated in MH broth.

| Peptide | SEQ ID NO: | Sequence | DOI[1] (mm) | MIC$_{50}$ (µM) | MIC$_{\%}$[2] (%) |
|---|---|---|---|---|---|
| 1 | 11 | KRKKHRCRVYNNGMPTGMYRWC | 15 | 4.01 | 25 |
| 2 | 12 | KRKKHRCRVYNNGLPTGLYRWC | 15 | 2.00 | 50 |
| 3 | 13 | KRKKHRCRVYNNGLPTGLYRWC-NH$_2$ | 13 | 1.02 | 100 |
| 4 | 14 | Ac-KRKKHRCRVYNNGLPTGLYRWC-NH$_2$ | 12 | 2.03 | 50 |
| 5 | 15 | ---KHRCRVYNNGLPTGLYRWC-NH$_2$ | 15 | 4.78 | 25 |
| 6 | 16 | ----HRCRVYNNGLPTGLYRWC-NH$_2$ | 11 | 10.1 | 12.5 |
| 7 | 17 | -----RCRVYNNGLPTGLYRWC-NH$_2$ | 10 | 21.6 | 6.25 |
| 8 | 18 | ------CRVYNNGLPTGLYRWC-NH$_2$ | n.a.[3] | 187 | 0.78 |
| 9 | 19 | KRKKHRCRVFNNGLPTGLYRWC-NH$_2$ | 10 | 4.08 | 25 |
| 10 | 20 | KRKKHRCRVWNNGLPTGLYRWC-NH$_2$ | 9 | 8.05 | 12.5 |
| 11 | 21 | KRKKHRCRVYNNGLPTGLFRWC-NH$_2$ | 12 | 1.02 | 100 |
| 12 | 22 | KRKKHRCRVYNNGLPTGLSRWC-NH$_2$ | 12 | 2.09 | 50 |
| 13 | 23 | KRKKHRCRVYNNGLPTGLWRWC-NH$_2$ | 12 | 2.01 | 50 |
| K1A | 24 | ARKKHRCRVYNNGLPTGLYRWC-NH$_2$ | 13 | 1.02 | 100 |
| R2A | 25 | KAKKHRCRVYNNGLPTGLYRWC-NH$_2$ | 14 | 2.03 | 50 |
| K3A | 26 | KRAKHRCRVYNNGLPTGLYRWC-NH$_2$ | 12 | 1.02 | 100 |
| K4A | 27 | KRKAHRCRVYNNGLPTGLYRWC-NH$_2$ | 12 | 4.06 | 25 |

TABLE 4-continued

Bactofencin A and variants thereof and their activity against
S. aureus ATCC 6538 cultivated in MH broth.

| Peptide | SEQ ID NO: | Sequence | DOI[1] (mm) | $MIC_{50}$ (μM) | $MIC_{\%}$[2] (%) |
|---|---|---|---|---|---|
| H5A  | 28 | KRKKARCRVYNNGLPTGLYRWC-NH$_2$ | 11 | 2.03 | 50 |
| R6A  | 29 | KRKKHACRVYNNGLPTGLYRWC-NH$_2$ | 12 | 2.03 | 50 |
| C7A  | 30 | KRKKHRARVYNNGLPTGLYRWC-NH$_2$ | 8  | 16.25 | 6.25 |
| R8A  | 31 | KRKKHRCAVYNNGLPTGLYRWC-NH$_2$ | 11 | 4.06 | 25 |
| V9A  | 32 | KRKKHRCRAYNNGLPTGLYRWC-NH$_2$ | 9  | 32.50 | 3.13 |
| Y10A | 33 | KRKKHRCRVANNGLPTGLYRWC-NH$_2$ | 8  | 32.50 | 3.13 |
| N11A | 34 | KRKKHRCRVYANGLPTGLYRWC-NH$_2$ | 8  | 16.25 | 6.25 |
| N12A | 35 | KRKKHRCRVYNAGLPTGLYRWC-NH$_2$ | 8  | 8.12 | 12.5 |
| G13A | 36 | KRKKHRCRVYNNALPTGLYRWC-NH$_2$ | 8  | 32.50 | 3.13 |
| L14A | 37 | KRKKHRCRVYNNGAPTGLYRWC-NH$_2$ | 9  | 16.25 | 6.25 |
| P15A | 38 | KRKKHRCRVYNNGLATGLYRWC-NH$_2$ | 10 | 4.06 | 25 |
| T16A | 39 | KRKKHRCRVYNNGLPAGLYRWC-NH$_2$ | 8  | 64.99 | 1.56 |
| G17A | 40 | KRKKHRCRVYNNGLPTALYRWC-NH$_2$ | 9  | 8.12 | 12.5 |
| L18A | 41 | KRKKHRCRVYNNGLPTGAYRWC-NH$_2$ | 11 | 4.06 | 25 |
| Y19A | 42 | KRKKHRCRVYNNGLPTGLARWC-NH$_2$ | 12 | 64.99 | 1.56 |
| R20A | 43 | KRKKHRCRVYNNGLPTGLYAWC-NH$_2$ | 12 | 32.50 | 3.13 |
| W21A | 44 | KRKKHRCRVYNNGLPTGLYRAC-NH$_2$ | 11 | 4.06 | 25 |
| C22A | 45 | KRKKHRCRVYNNGLPTGLYRWA-NH$_2$ | n.a. | n.a. | n.a. |

[1]DOI = Diameter of inhibition;
[2]MIC$_\%$ = % of inhibition is based on analog 3 used for ala-scan;
[3]n.a. = no activity observed at tested concentrations of 1 mg/mL.

Leucine for methionine substitution resulted in variants having increased activity. Indeed, enhanced activity was observed for peptide 2 relative to peptide 1 (2.00 μM versus 4.06 M respectively) against *S. aureus*. Substituting the HMPB linker for the Rink linker resulted in the isolation of peptides (following cleavage from the solid state resin) having an amidated C-terminal. In an embodiment of the present disclosure, bactofencin A-based variants were prepared comprising an acetylated N-terminal (e.g. peptide 4). Peptide 3 comprising an amidated C-terminal was shown to exhibit enhanced activity relative to peptides 1 and 2 respectively against *S. aureus*. However, peptide 4, comprising both an amidated C-terminal and an acetylated N-terminal, was shown to exhibit an activity against *S. aureus* similar to peptide 2. Substitution of the HMPB-ChemMatrix for the 2-TCP resin, resulted in higher yields of isolated peptides (25.8% to 62.6% respectively) following purification. Peptide 2, obtained by replacement of the methionine residues for leucine residues, was shown to exhibit better activity against both *S. aureus* and *L. monocytogenes*, suggesting that the methionine residues can be replaced in order to enhance the oxidative resistance of the peptide. Cysteine replacement resulted in 6.25% activity for peptide C7A and a complete loss of activity for peptide C22A. Various alanine substitutions, as for peptides K1A-C22A were also performed. The intramolecular disulfide bond seems to be essential for the activity. Indeed, substitution of the cysteine residues at positions 7 and 22 respectively resulted in an important loss of activity for C7A to complete inactivation for C22A respectively. The loss of activity observed for peptides wherein one or both of the cysteine residues have been substituted further emphasizes the importance of in situ disulfide bond formation in the activity of the peptides. Moreover, in situ disulfide bond formation is further corroborated by the activity observed for the use of linear peptides comprising cysteine residues in a biological medium.

EXPERIMENTAL

A number of examples are provided herein below illustrating the process for the linear synthesis of gram-positive class II bacteriocins and compositions and uses thereof. In accordance with various embodiments of the present disclosure, a number of examples are provided hereinbelow illustrating the linear solid support peptide synthesis of pediocin PA-1 and compositions and uses thereof. In accordance with various embodiments of the present disclosure, a number of examples are provided hereinbelow illustrating the linear solid support peptide synthesis of bactofencin A and compositions and uses thereof. The following non-limiting examples are illustrative of the present disclosure.

Example 1: Materials

All reagents and solvents were purchased from commercial suppliers and used without further purification. Fmoc amino acid derivatives, coupling reagents (e.g. 2-(7-aza-1H-benzotriazole-1-yl)-1,1,3,3-tetramethyluronium hexafluorophosphate (HATU), 2-(1H-benzotriazol-1-yl)-1,1,3,3-tetramethyluronium hexafluorophosphate (HBTU), 2-(6-chloro-1H-benzotriazole-1-yl)-1,1,3,3-tetramethylammonium hexafluorophosphate (HCTU) and 1-(mesitylene-2-sulfonyl)-3-nitro-1,2,4-triazole (MSNT) were purchased from Matrix innovation (Quebec, QC, Canada). Aminomethyl-ChemMatrix® resin (0.69 mmol/g) was purchased from PCAS Biomatrix Inc. (St-Jean-sur-Richelieu, QC, Canada). Pseudoproline derivatives were purchased from Gyros Protein Technologies (Tucson, Ariz., USA). Linker 4-(4-hydroxymethyl-3-methoxyphenoxy)-butyric acid (HMPBA) was purchased from Chem-Impex (Wood Dale, Ill., USA). Other reagents and solvents were purchased from Sigma-Aldrich.

Example 2: Analytical Analyses

LC/MS analyses were conducted on a Shimadzu Prominence LCMS-2020 system equipped with an ElectroSpray Ionization (ESI) probe and using a Kinetex® column (4.6 mm×100 mm, 2.6 m XB-C18, 100 Å, 1.8 mL/min) and a 10.5 min. gradient from water (0.1% HCOOH) and $CH_3CN$ (0.1% HCOOH) ($CH_3CN$ 10-100%) and detection at 220 nm and 254 nm. High Resolution Mass Spectrometry (HRMS) was performed on a Waters Synapt G2-Si (Quadrupole/TOF) equipped with a Waters UPLC binary pump and an FTN (Flow-Through Needle) injector. The mass spectrometer was operated in High resolution mode; calibration was performed using a sodium formate solution; and lock-mass correction was performed using a Leucine-enkephalin solution (Waters). Matrix-Assisted Laser Desorption Ionization Time-of-Flight (MALDI-TOF) mass spectrometry was performed using a AB SCIEX 4800 Plus MALDI-TOF/TOF® instrument equipped with an alpha-cyano-4-hydroxycinnamic acid matrix. The spectra were acquired using the 4000 Series Explorer Software (Ab Sciex, v 3.2.3). The PEAKS Studio software (Bioinformatics Solutions, v.7.0) was used for spectra analysis and DENOVO sequencing.

Example 3: Peptide Synthesis

Peptides were synthesized by standard Fmoc solid-phase synthesis with appropriate orthogonal protection and resin linker strategies using a Prelude automated peptide synthesizer from Gyros Protein Technologies (Tucson, Ariz., USA) and an HMPB-ChemMatrix® resin. The HMPB-ChemMatrix resin was prepared by swelling aminomethyl-ChemMatrix in DMF for 1 h followed by the addition of 4-(4-hydroxymethyl-3-methoxyphenoxy)-butyric acid (HMPBA) (3 equiv.), HBTU (3 equiv.), HOBt (3 equiv.) and N-methylmorpholine (NMM) (6 equiv.) respectively. After stirring the mixture for 3 h, the resin was washed with DMF (dimethylformamide) (5×) and DCM (dichloromethane) (5×) and dried under vacuum. The C-terminal amino acid was subsequently attached by dissolving Fmoc-Cys(Trt)-OH (5 equiv.) in DCM with a minimum amount of anhydrous THF, and adding the resulting solution to the previously prepared resin swollen in DCM. MSNT (1-(mesitylene-2-sulfonyl)-3-nitro-1,2,4-triazole) (5 equiv.) and N-methylimidazole (3.75 equiv.) were dissolved in DCM and incubated with the resin for 1 h under agitation. After washing the resin with DCM (5×) and DMF (5×), peptide elongation was carried out by standard Fmoc solid phase peptide synthesis: the Fmoc protecting group was removed from the resin by two 10 min treatments with 20% piperidine in DMF (v/v); and amino acid couplings were performed using Fmoc-Xaa-OH (3 equiv.), HCTU (3 equiv.) and NMM (12 equiv.) in DMF (2×30 min). Cleavage, side chain deprotection, and pseudoproline ring reopening were respectively achieved by treatment with TFA/TIPS (triisopropylsilane)/$H_2O$/phenol (90:5:2.5:2.5) over a period of 1 h. After precipitation in cold ether, a second side chain deprotection treatment using TFA/TIPS/$H_2O$ (95:2.5:2.5) was performed to ensure complete deprotection and pseudoproline ring opening. The resulting peptide was subsequently precipitated using cold diethyl ether, washed twice with diethyl ether and dried under vacuum. Finally, the peptide was purified by RP-HPLC (Reversed phase HPLC) using a Shimadzu Prominence instrument equipped with a Phenomenex Kinetex® EVO C18 column (250 mm×21.2 mm, 5.0 μm, 300 Å) and using 0.1% AcOH/$H_2O$ (solvent A) and 0.1% AcOH/$CH_3CN$ (solvent B) with a linear gradient of 5% to 50% (for solvent B) over a period of 20 min at 14 ml/min and UV detection at 220 and 254 nm respectively. The collected fractions were subsequently freeze-dried to afford the desired peptide as a white powder.

Example 4: Disulfide Bond Formation

The purified linear peptide was dissolved in $CH_3CN$/$H_2O$ (1:1) at a concentration of 1 mg/mL and cyclized by the addition of NCS (N-chlorosuccinimide) (4 equiv. or 2 equiv. per disulfide bond). After stirring for 30 min, the cyclized peptide product was freeze-dried and purified by RP-HPLC as described hereinabove.

Example 5: Selective Methionine Reduction

Selective methionine sulfoxide reduction (oxidized Met) was carried out by treating the peptide at a concentration of 1 mg/mL with TBAB (tetrabutylammonium bromide) (30 equiv.) and TFA/β-mercaptoethanol/anisole (95:2.5:2.5) over a period of 5 min while at room temperature, followed by precipitation and washing using cold diethyl ether. The resulting peptide product was subsequently characterized by RP-HPLC and matrix-assisted laser desorption ionization time-of-flight mass spectrometry (MALDI-TOF).

Example 6: Antimicrobial Assays

The antibacterial activity of the synthetic peptides in accordance with an embodiment of the present disclosure, was assessed by radial diffusion assays against *L. monocytogenes* LSD530 from the Canadian Food Inspection Agency (Laboratory Services Division, Ottawa, ON, Canada), *L. monocytogenes* ATCC 19111 and *M. luteus* 10240 from the American Type Culture Collection (Rockville, Md., USA), *P. acidilacti* UL5 from the STELA Dairy Research Center culture collection (Université Laval, QC, Canada), and *Listeria ivanovii* HPB28 (Health Protection Branch, Health and Welfare, Ottawa, ON, Canada). A sample (80 IL) containing 1 mg/mL of purified peptide was applied into the hole of a MRS (Oxoid, Nepean, ON, Canada) or TSBYE soft agar (0.75% w/v) overlay seeded with the producer strain *P. acidilacti* and the indicator strain of *L. monocytogenes* LSD530. The petri plates (100×15 mm) (VWR, Radnor, Pa., USA) were incubated at 35° C. for 18 h and the antibacterial activity was observed as a halo of inhibition formed in the bacterial carpet around the sample of the indicator strain. Nisin supernatant was obtained from *Lactococcus lactis* subsp. *lactis* ATCC 11454 in MRS broth at 30° C. after 18 h. All strains were reactivated from 20% glycerol stock at −80° C. and sub-cultured at least three times at 24 h intervals before use. Pictures were taken using the ChemiDoc® XRS imaging system (Bio-Rad, Hercules, Calif., USA).

The minimal inhibitory concentrations (MIC) of the synthetic peptides were determined using 96-well Falcon® polystyrene micro-assay plates (Corning, N.Y., USA). Micro-plates loaded with twofold serial dilutions of each peptide (starting at 250 μM) in tryptic soy broth (Difco Laboratories, Sparks, Md., USA) supplemented with 0.6% yeast extract (w/v) were seeded with log-phase culture of target strain diluted in TSBYE to $0.5-1.0\times10^6$ cfu mL$^{-1}$ (approximately $1\times10^4$ cfu per well). The micro-plates were then incubated at 30° C. for 18 h and the absorbance at 595 nm was measured hourly using an Infinite® F200 PRO photometer (Tecan US, Inc., Durham, N.C., USA). The MIC values were expressed in M and correspond to the lowest concentration that inhibited the growth of the target organism after 18 h. The MIC values are reported as means of two independent experiments performed in duplicate.

The skim milk experiment was done in a preparation of 12% sterilized skim milk. *L. monocytogenes* ATCC 19111 was inoculated at approximately 106 cfu/mL. Serial dilutions were performed and the cfus counted after 2, 4, 6, 8, 10 12, 24 and 48 h using 20 μL for each replicate from each dilution on TSBYE agar plate (1.25% w/v) and incubated for 24 h.

Example 7: Circular Dichroism (Cd)

Peptides were dissolved in 0.1% TFA/H$_2$O (1 mg/mL) and diluted to 0.1 mM in aqueous TFE solutions (0, 25, 50, 75 or 90% TFE in H$_2$O). For the study in phospholipid vesicles, a lipid/peptide ratio of 100:1 was used. DMPC (dimyristoylphophatidylcholine) or DMPG (dimyristoylphophatidylglycerol) was dissolved in MeOH and the mixture dried with a stream of nitrogen. The peptides were subsequently dissolved in phosphate buffer (20 mM, pH 7.4) (1 mg/mL) and added to the dried phospholipid films. Finally, the micelles were sonicated for 5 min or until a clear solution was obtained. CD measurements of the peptides in aqueous TFE solutions and in phospholipid vesicles were performed using a Jasco J-815 Circular Dichroism Spectropolarimeter (Aviv Instruments, Lakewood, N.J., USA). The spectra were recorded at 25° C. in the 190-260 nm wavelength range, at 0.1 nm intervals, in a cuvette with a 0.1 mm path length. For each spectrum, ten scans were averaged and smoothed using the J720/98 system program (Version 120C). CD data were expressed as mean residue molar ellipticity [θ] expressed in deg cm$^2$ dmol$^{-1}$, plotted against wavelength (nm) and analyzed using the CONTIN algorithm included in the CDPro analysis software.

Example 8: NMR Spectroscopy

Samples were prepared using 2 mg of Pediocin PA-1, 3c, and ped[M31L] 5 dissolved in a solution of H$_2$O with 0.1% TFA (300VL) and TFE-d2 98% (300 L) in a 3 mm Wilmad NMR tube obtained from Rototec-Spintec. Experiments were performed using a Bruker Avance 600 MHz spectrometer equipped with a cryoprobe. The temperature effect on the structure was surveyed by recording $^1$H NMR spectra at variable temperatures (288, 298, 303, 308, 313° K) and water suppression using sculpting with gradients. For sequential assignments, TOCSY and NOESY experiments were performed in phase-sensitive mode. TOCSY and NOESY spectra were recorded with mixing times of 80 ms and 300 ms respectively at 313° K and for 16 and 72 scans respectively. Water suppression was achieved using excitation sculpting. All spectra were processed with Bruker TOPSPIN® 3.5 software.

Example 9: In Situ Disulfide Bond Formation

Incorrect disulfide bond pairings such as in analogs 3a and 3b reduced inhibitory activity. These results suggest that the disulfide bonds may exist in a dynamic equilibrium that allows for some remodeling in the culture medium to produce a small quantity of the bioactive conformation. Surprisingly, equivalent antimicrobial activities were observed for linear analogs 1 and 4 in radial diffusion and microplate dilution assays (Table 2). These results support the in situ disulfide bond formation hypothesis proposing that suitable disulfide bonds can be formed in the bioassay medium without the help of chaperone-like proteins.[5] Based on the disulfide bond pairing ratios of 2a (7.5%), 2b (21.5%) and 2c (71.0%) obtained after cyclization with NCS and the similar antimicrobial activities, a similar equilibrium could be reached in culture medium containing linear analogues 1 and 4 but also native pediocin PA-1 3c. Substitution of all four cysteine residues with alanine showed that the disulfide bonds are essential for pediocin PA-1 activity, since linear analog 6 was inactive which lends further support for in situ disulfide bond of the linear analogues.

While the present disclosure has been described with reference to illustrative examples, it is to be understood that the disclosure is not limited to the disclosed examples. To the contrary, the disclosure is intended to cover various modifications and equivalent arrangements included within the spirit and scope of the appended claims.

REFERENCES REFERRED TO IN THE SPECIFICATION

1. Cotter, P. D.; Ross, R. P.; Hill, C., Bacteriocins—a viable alternative to antibiotics? *Nature reviews. Microbiology* 2013, 11 (2), 95-105.
2. Abee, T.; Krockel, L.; Hill, C., Bacteriocins: modes of action and potentials in food preservation and control of food poisoning. *International journal of food microbiology* 1995, 28 (2), 169-85.
3. Bastos Mdo, C.; Coelho, M. L.; Santos, O. C., Resistance to bacteriocins produced by Gram-positive bacteria. *Microbiology* 2015, 161 (Pt 4), 683-700.
4. Duhan, J. S.; Nehra, K.; Gahlawat, S. K.; Saharan, P.; Surekha, D., Bacteriocins from Lactic Acid Bacteria. *Biotechnology: Prospects and Applications*, Salar, R. K.; Gahlawat, S. K.; Siwach, P.; Duhan, J. S., Eds. Springer India: New Delhi, 2013; pp 127-141.
5. Wolska, K. I.; Grzes, K.; Kurek, A., Synergy between novel antimicrobials and conventional antibiotics or bacteriocins. *Pol J Microbiol* 2012, 61 (2), 95-104.
6. Pattabiraman, V. R.; Bode, J. W., Rethinking amide bond synthesis. *Nature* 2011, 480 (7378), 471-9.
7. O'Bryan, C. A.; Koo, O. K.; Sostrin, M. L.; Ricke, S. C.; Crandall, P. G.; Johnson, M. G., Chapter 15—Characteristics of Bacteriocins and Use as Food Antimicrobials in the United States. In *Food and Feed Safety Systems and Analysis*, Academic Press: 2018; pp 273-286.

8. Derksen, D. J.; Boudreau, M. A.; Vederas, J. C., Hydrophobic interactions as substitutes for a conserved disulfide linkage in the type IIa bacteriocins, leucocin A and pediocin PA-1. *Chembiochem: a European journal of chemical biology* 2008, 9 (12), 1898-901.
9. Oppegard, C.; Fimland, G.; Anonsen, J. H.; Nissen-Meyer, J., The Pediocin PA-1 Accessory Protein Ensures Correct Disulfide Bond Formation in the Antimicrobial Peptide Pediocin PA-1. *Biochemistry* 2015, 54 (19), 2967-2974.
10. Johnsen, L.; Fimland, G.; Eijsink, V.; Nissen-Meyer, J., Engineering increased stability in the antimicrobial peptide pediocin PA-1. *Applied and environmental microbiology* 2000, 66 (11), 4798-802.
11. Tiwari, S. K.; Sutyak Noll, K.; Cavera, V. L.; Chikindas, M. L., Improved antimicrobial activities of synthetic-hybrid bacteriocins designed from enterocin E50-52 and pediocin PA-1. *Applied and environmental microbiology* 2015, 81 (5), 1661-7.
12. O'Shea, E. F.; O'Connor, P. M.; O'Sullivan, O.; Cotter, P. D.; Ross, R. P.; Hill, C., Bactofencin A, a new type of cationic bacteriocin with unusual immunity. *mBio* 2013, 4 (6), e00498-13.

---

The invention claimed is:

1. A process for the linear synthesis of a bacteriocin or a variant thereof, the process comprising:
   stepwise addition of selected amino acids to a solid support;
   pseudoproline positioning and reopening;
   cleavage of the bacteriocin or the variant thereof from the solid support to provide a linear bacteriocin or variant thereof;
   adding the linear bacteriocin to a pharmaceutically acceptable carrier to obtain a composition; and
   applying the composition to a food matrix comprising a disulfide bond containing protein,
   wherein in situ disulfide bond formation occurs in the linear bacteriocin when the linear bacteriocin contacts the food matrix, and wherein the disulfide bond formation comprises oxidative coupling of a pair of thiol containing amino acid residues present in the linear bacteriocin.

2. The process of claim 1, further comprising treating the linear bacteriocin or variant thereof with a mobile phase comprising an acid.

3. The process of claim 1, wherein the pair of thiol containing amino acid residues comprises at least one of cysteine or homocysteine.

4. The process of claim 1, wherein the solid support is selected from the group consisting of a ChemMatrix resin, a Wang resin, a polystyrene resin, a substituted polystyrene-based resin, a polyamide resin, a polyacrylate resin, a polyacrylamide resin, and a polyethylene glycol-based resin.

5. The process of claim 4, wherein the solid support further comprises a resin linker.

6. The process of claim 5, wherein the resin linker is an HMPB linker, a Wang linker, a Rink amide linker, a PAL linker, a Ramage linker, a Sieber linker, a linker comprising an hydroxyl function or a trityl-based linker.

7. The process of claim 2, wherein the acid comprises at least acetic acid.

8. The process of claim 1, wherein the bacteriocin or variant thereof is a gram-positive class IIa bacteriocin or a variant thereof, a gram-positive class IIb bacteriocin or a variant thereof, a gram-positive class IIc bacteriocin or a variant thereof or a gram-positive class IId bacteriocin or a variant thereof.

9. The process of claim 8, wherein the gram-positive class IIa bacteriocin or variant thereof is a pediocin-like bacteriocin or variant thereof; and wherein the gram-positive class IId bacteriocin or variant thereof is a bactofencin-like bacteriocin or variant thereof.

10. The process of claim 1, wherein the variant has at least 80% sequence identity with an unmodified or native reference sequence.

11. The process of claim 1, wherein the variant has at least one of an amino acid substitution, modification, addition or deletion relative to an unmodified or native reference sequence.

12. The process of claim 11, wherein the amino acid substitution comprises substituting at least one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine or tryptophan for any one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine or tryptophan.

13. The process of claim 12, wherein the amino acid substitution comprises substituting at least one of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine or tryptophan for alanine, leucine, phenylalanine, tryptophan, or serine.

14. The process of claim 13, wherein the amino acid substitution comprises substituting at least one of lysine, arginine, histidine, cysteine, valine, tyrosine, asparagine, glycine, methionine, proline, threonine, tryptophan or cysteine for alanine.

15. The process of claim 13, wherein the amino acid substitution comprises substituting methionine for leucine.

16. The process of claim 13, wherein the amino acid substitution comprises substituting tyrosine for phenylalanine, serine or tryptophan.

17. The process of claim 1, wherein the bacteriocin or variant thereof is at least one of bavaricin, helveticin, acidocin, lactocin, lactacin, lacticin, leucocin, lactococcin, pediocin, curvaticin, curvacin, mutacin, mesentericin, plantaricin, streptin, sakacin or variants thereof.

18. The process of claim 1, wherein the linear bacteriocin or variant thereof is not purified after in situ disulfide bond formulation.

* * * * *

SEQUENCE LISTING

<160> NUMBER OF SEQ ID NOS: 45

<210> SEQ ID NO 1
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 1

Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 2
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (9)..(14)
<220> FEATURE:
<221> NAME/KEY: DISULFID
<222> LOCATION: (24)..(44)
<220> FEATURE:
<221> NAME/KEY: MISC_FEATURE
<222> LOCATION: (31)..(31)
<223> OTHER INFORMATION: Methionine sulfoxide

<400> SEQUENCE: 2

Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 3
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (9)..(24)
<220> FEATURE:
<221> NAME/KEY: DISULFID
<222> LOCATION: (14)..(44)

<400> SEQUENCE: 3

Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 4
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (9)..(44)
<220> FEATURE:
<221> NAME/KEY: DISULFID
<222> LOCATION: (14)..(24)

<400> SEQUENCE: 4

Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 5
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (9)..(14)
<220> FEATURE:
<221> NAME/KEY: DISULFID
<222> LOCATION: (24)..(44)

<400> SEQUENCE: 5

Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40

<210> SEQ ID NO 6
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 6

Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Leu Ala
            20                  25                  30

```
Trp Ala Thr Gly Gly His Gln Gly Asn His Lys Cys
        35                  40
```

<210> SEQ ID NO 7
<211> LENGTH: 44
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (9)..(14)
<220> FEATURE:
<221> NAME/KEY: DISULFID
<222> LOCATION: (24)..(44)

<400> SEQUENCE: 7

```
Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Leu Ala
            20                  25                  30

Trp Ala Thr Gly Gly His Gln Gly Asn His Lys Cys
        35                  40
```

<210> SEQ ID NO 8
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 8

```
Lys Tyr Tyr Gly Asn Gly Val Thr Ala Gly Lys His Ser Ala Ser Val
1               5                   10                  15

Asp Trp Gly Lys Ala Thr Thr Ala Ile Ile Asn Asn Gly Ala Met Ala
            20                  25                  30

Trp Ala Thr Gly Gly His Gln Gly Asn His Lys Ala
        35                  40
```

<210> SEQ ID NO 9
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 9

```
Lys Arg Lys Lys His Arg Cys Arg Val Tyr Asn Asn Gly Met Pro Thr
1               5                   10                  15

Gly Met Tyr Arg Trp Cys
            20
```

<210> SEQ ID NO 10
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 10

```
Lys Arg Lys Lys His Arg Cys Arg Val Tyr Asn Asn Gly Leu Pro Thr
1               5                   10                  15

Gly Leu Tyr Arg Trp Cys
            20
```

```
<210> SEQ ID NO 11
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 11

Lys Arg Lys Lys His Arg Cys Arg Val Tyr Asn Asn Gly Met Pro Thr
1               5                   10                  15

Gly Met Tyr Arg Trp Cys
            20

<210> SEQ ID NO 12
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 12

Lys Arg Lys Lys His Arg Cys Arg Val Tyr Asn Asn Gly Leu Pro Thr
1               5                   10                  15

Gly Leu Tyr Arg Trp Cys
            20

<210> SEQ ID NO 13
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 13

Lys Arg Lys Lys His Arg Cys Arg Val Tyr Asn Asn Gly Leu Pro Thr
1               5                   10                  15

Gly Leu Tyr Arg Trp Cys
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 14

Lys Arg Lys Lys His Arg Cys Arg Val Tyr Asn Asn Gly Leu Pro Thr
1               5                   10                  15

Gly Leu Tyr Arg Trp Cys
            20

<210> SEQ ID NO 15
```

```
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (19)..(19)
<223> OTHER INFORMATION: AMIDATION

<400> SEQUENCE: 15

Lys His Arg Cys Arg Val Tyr Asn Asn Gly Leu Pro Thr Gly Leu Tyr
1               5                   10                  15

Arg Trp Cys

<210> SEQ ID NO 16
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (18)..(18)
<223> OTHER INFORMATION: AMIDATION

<400> SEQUENCE: 16

His Arg Cys Arg Val Tyr Asn Asn Gly Leu Pro Thr Gly Leu Tyr Arg
1               5                   10                  15

Trp Cys

<210> SEQ ID NO 17
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (17)..(17)
<223> OTHER INFORMATION: AMIDATION

<400> SEQUENCE: 17

Arg Cys Arg Val Tyr Asn Asn Gly Leu Pro Thr Gly Leu Tyr Arg Trp
1               5                   10                  15

Cys

<210> SEQ ID NO 18
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (16)..(16)
<223> OTHER INFORMATION: AMIDATION

<400> SEQUENCE: 18

Cys Arg Val Tyr Asn Asn Gly Leu Pro Thr Gly Leu Tyr Arg Trp Cys
1               5                   10                  15

<210> SEQ ID NO 19
<211> LENGTH: 22
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MOD_RES
<222> LOCATION: (22)..(22)
<223> OTHER INFORMATION: AMIDATION

<400> SEQUENCE: 19

Lys Arg Lys Lys His Arg Cys Arg Val Phe Asn Asn Gly Leu Pro Thr
1               5                   10                  15

Gly Leu Tyr Arg Trp Cys
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 20

Lys Arg Lys Lys His Arg Cys Arg Val Trp Asn Asn Gly Leu Pro Thr
1               5                   10                  15

Gly Leu Tyr Arg Trp Cys
            20

<210> SEQ ID NO 21
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 21

Lys Arg Lys Lys His Arg Cys Arg Val Tyr Asn Asn Gly Leu Pro Thr
1               5                   10                  15

Gly Leu Phe Arg Trp Cys
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 22

Lys Arg Lys Lys His Arg Cys Arg Val Tyr Asn Asn Gly Leu Pro Thr
1               5                   10                  15

Gly Leu Ser Arg Trp Cys
            20

<210> SEQ ID NO 23
<211> LENGTH: 22
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 23

Lys Arg Lys Lys His Arg Cys Arg Val Tyr Asn Asn Gly Leu Pro Thr
1               5                   10                  15

Gly Leu Trp Arg Trp Cys
            20

<210> SEQ ID NO 24
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 24

Ala Arg Lys Lys His Arg Cys Arg Val Tyr Asn Asn Gly Leu Pro Thr
1               5                   10                  15

Gly Leu Tyr Arg Trp Cys
            20

<210> SEQ ID NO 25
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 25

Lys Ala Lys Lys His Arg Cys Arg Val Tyr Asn Asn Gly Leu Pro Thr
1               5                   10                  15

Gly Leu Tyr Arg Trp Cys
            20

<210> SEQ ID NO 26
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 26

Lys Arg Ala Lys His Arg Cys Arg Val Tyr Asn Asn Gly Leu Pro Thr
1               5                   10                  15

Gly Leu Tyr Arg Trp Cys
            20

<210> SEQ ID NO 27
<211> LENGTH: 22
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 27

Lys Arg Lys Ala His Arg Cys Arg Val Tyr Asn Asn Gly Leu Pro Thr
1               5                   10                  15

Gly Leu Tyr Arg Trp Cys
            20

<210> SEQ ID NO 28
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 28

Lys Arg Lys Lys Ala Arg Cys Arg Val Tyr Asn Asn Gly Leu Pro Thr
1               5                   10                  15

Gly Leu Tyr Arg Trp Cys
            20

<210> SEQ ID NO 29
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 29

Lys Arg Lys Lys His Ala Cys Arg Val Tyr Asn Asn Gly Leu Pro Thr
1               5                   10                  15

Gly Leu Tyr Arg Trp Cys
            20

<210> SEQ ID NO 30
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 30

Lys Arg Lys Lys His Arg Ala Arg Val Tyr Asn Asn Gly Leu Pro Thr
1               5                   10                  15

Gly Leu Tyr Arg Trp Cys
            20

<210> SEQ ID NO 31
<211> LENGTH: 22
<212> TYPE: PRT
```

<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 31

Lys Arg Lys Lys His Arg Cys Ala Val Tyr Asn Asn Gly Leu Pro Thr
1               5                   10                  15

Gly Leu Tyr Arg Trp Cys
            20

<210> SEQ ID NO 32
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 32

Lys Arg Lys Lys His Arg Cys Arg Ala Tyr Asn Asn Gly Leu Pro Thr
1               5                   10                  15

Gly Leu Tyr Arg Trp Cys
            20

<210> SEQ ID NO 33
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 33

Lys Arg Lys Lys His Arg Cys Arg Val Ala Asn Asn Gly Leu Pro Thr
1               5                   10                  15

Gly Leu Tyr Arg Trp Cys
            20

<210> SEQ ID NO 34
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 34

Lys Arg Lys Lys His Arg Cys Arg Val Tyr Ala Asn Gly Leu Pro Thr
1               5                   10                  15

Gly Leu Tyr Arg Trp Cys
            20

<210> SEQ ID NO 35
<211> LENGTH: 22

<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 35

Lys Arg Lys Lys His Arg Cys Arg Val Tyr Asn Ala Gly Leu Pro Thr
1               5                   10                  15

Gly Leu Tyr Arg Trp Cys
            20

<210> SEQ ID NO 36
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 36

Lys Arg Lys Lys His Arg Cys Arg Val Tyr Asn Asn Ala Leu Pro Thr
1               5                   10                  15

Gly Leu Tyr Arg Trp Cys
            20

<210> SEQ ID NO 37
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 37

Lys Arg Lys Lys His Arg Cys Arg Val Tyr Asn Asn Gly Ala Pro Thr
1               5                   10                  15

Gly Leu Tyr Arg Trp Cys
            20

<210> SEQ ID NO 38
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 38

Lys Arg Lys Lys His Arg Cys Arg Val Tyr Asn Asn Gly Leu Ala Thr
1               5                   10                  15

Gly Leu Tyr Arg Trp Cys
            20

<210> SEQ ID NO 39

```
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 39

Lys Arg Lys Lys His Arg Cys Arg Val Tyr Asn Asn Gly Leu Pro Ala
1               5                   10                  15

Gly Leu Tyr Arg Trp Cys
            20

<210> SEQ ID NO 40
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 40

Lys Arg Lys Lys His Arg Cys Arg Val Tyr Asn Asn Gly Leu Pro Thr
1               5                   10                  15

Ala Leu Tyr Arg Trp Cys
            20

<210> SEQ ID NO 41
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 41

Lys Arg Lys Lys His Arg Cys Arg Val Tyr Asn Asn Gly Leu Pro Thr
1               5                   10                  15

Gly Ala Tyr Arg Trp Cys
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 42

Lys Arg Lys Lys His Arg Cys Arg Val Tyr Asn Asn Gly Leu Pro Thr
1               5                   10                  15

Gly Leu Ala Arg Trp Cys
            20
```

```
<210> SEQ ID NO 43
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 43

Lys Arg Lys Lys His Arg Cys Arg Val Tyr Asn Asn Gly Leu Pro Thr
1               5                   10                  15

Gly Leu Tyr Ala Trp Cys
            20

<210> SEQ ID NO 44
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 44

Lys Arg Lys Lys His Arg Cys Arg Val Tyr Asn Asn Gly Leu Pro Thr
1               5                   10                  15

Gly Leu Tyr Arg Ala Cys
            20

<210> SEQ ID NO 45
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (22)..(22)
<223> OTHER INFORMATION: AMIDATION

<400> SEQUENCE: 45

Lys Arg Lys Lys His Arg Cys Arg Val Tyr Asn Asn Gly Leu Pro Thr
1               5                   10                  15

Gly Leu Tyr Arg Trp Ala
            20
```